(12) United States Patent
Scherer et al.

(10) Patent No.: US 11,732,037 B2
(45) Date of Patent: *Aug. 22, 2023

(54) WEIGHT LOSS REGIMEN

(71) Applicant: Board of Regents, The University of Texas System, Austin, TX (US)

(72) Inventors: Philipp E. Scherer, Dallas, TX (US); Shangang Zhao, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 169 days.

This patent is subject to a terminal disclaimer.

(21) Appl. No.: 17/124,483

(22) Filed: Dec. 16, 2020

(65) Prior Publication Data

US 2021/0395359 A1    Dec. 23, 2021

Related U.S. Application Data

(63) Continuation of application No. PCT/US2019/037223, filed on Jun. 14, 2019.

(60) Provisional application No. 62/685,996, filed on Jun. 16, 2018.

(51) Int. Cl.
*A61P 3/04* (2006.01)
*C07K 16/26* (2006.01)
*A61P 3/10* (2006.01)

(52) U.S. Cl.
CPC ............... *C07K 16/26* (2013.01); *A61P 3/04* (2018.01); *A61P 3/10* (2018.01)

(58) Field of Classification Search
CPC ............... C07K 16/26; A61P 3/04; A61P 3/10
See application file for complete search history.

(56) References Cited

U.S. PATENT DOCUMENTS

| | | | |
|---|---|---|---|
| 8,067,545 B2 * | 11/2011 | Grasso | A61K 48/00 530/387.9 |
| 2004/0048773 A1 | 3/2004 | Cawthorne et al. | |
| 2006/0079443 A1 * | 4/2006 | Ilan | A61K 38/2264 514/3.3 |

FOREIGN PATENT DOCUMENTS

WO    2019180272 A1    9/2019

OTHER PUBLICATIONS

Langeveld et al, Endocrine connections, Mar. 1, 2016, (abstract).*
Levy et al (PLOS one, Dec. 16, 2015).*
Mahmoudian et al. (Hybridoma, vol. 31: p. 372-377, 2012).*
Chamow and Ashkenazi, TIBTECH 14: 52-60, (1996).*
Maskari 2006, Correlation between Serum Leptin Levels, Body Mass Index and Obesity in Omanis, Sultan Qaboos University Medical Journal Dec. 2006 vol. 6, No. 2, Sultan Qaboos University.

* cited by examiner

*Primary Examiner* — Gyan Chandra
(74) *Attorney, Agent, or Firm* — Richard Aron Osman

(57) ABSTRACT

Obesity and/or diabetes are treated by partially inhibiting circulating leptin in a person in need thereof.

4 Claims, 14 Drawing Sheets

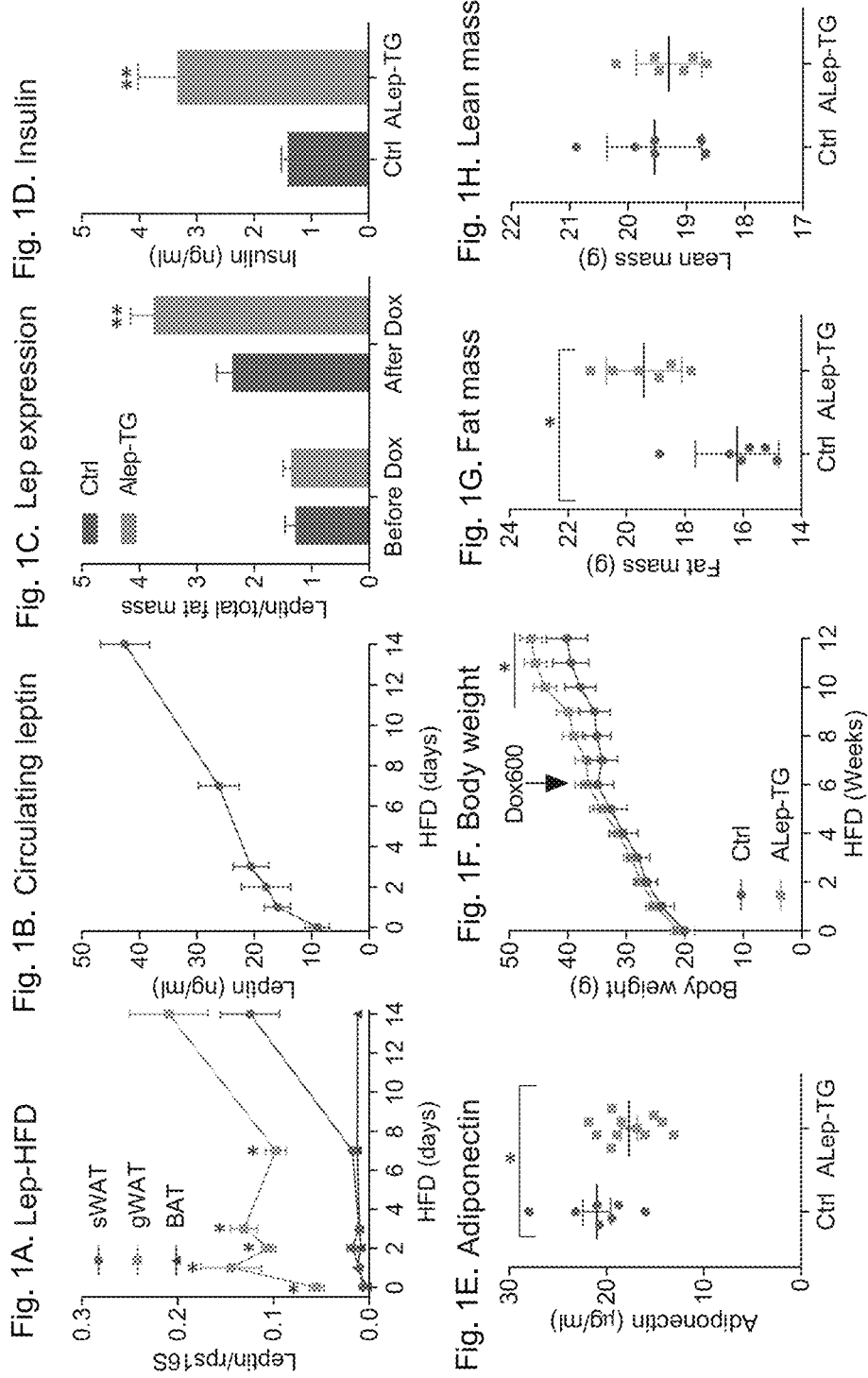

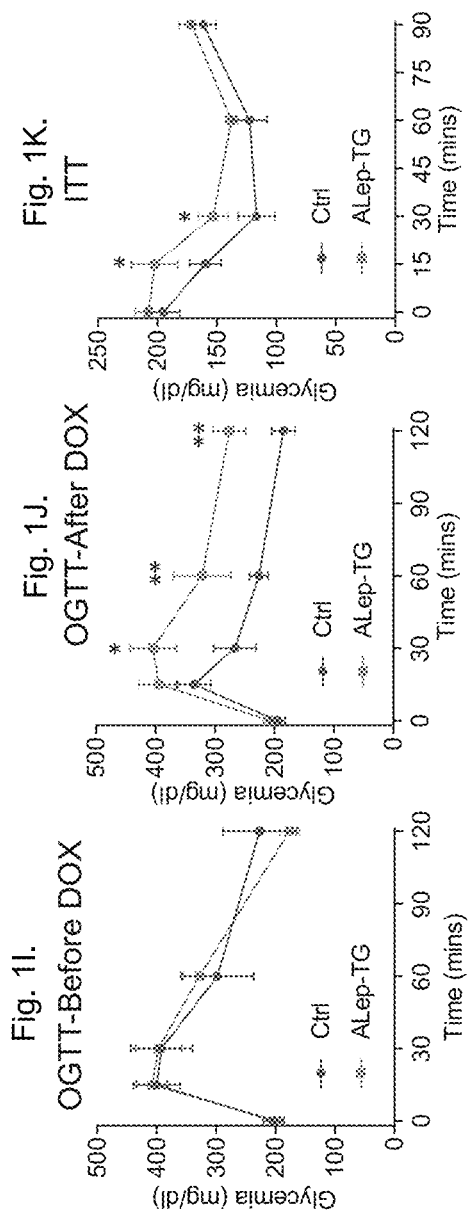
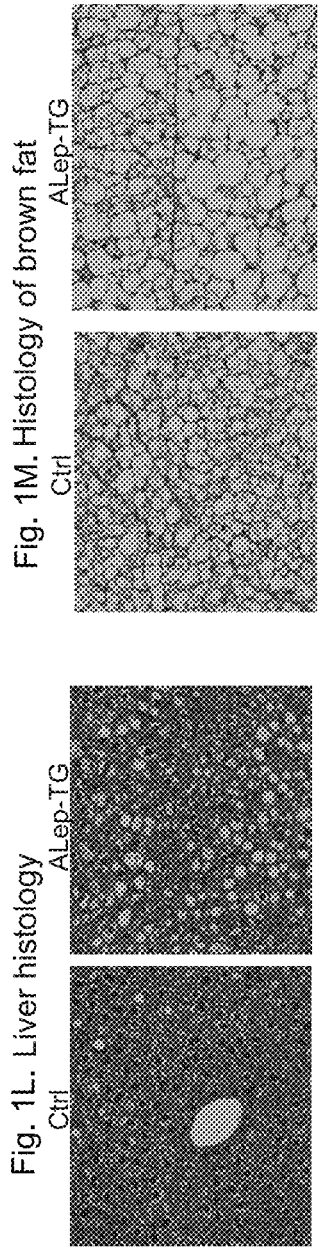
Fig. 1L. OGTT-Before DOX
Fig. 1J. OGTT-After DOX
Fig. 1K. ITT
Fig. 1L. Liver histology
Fig. 1M. Histology of brown fat

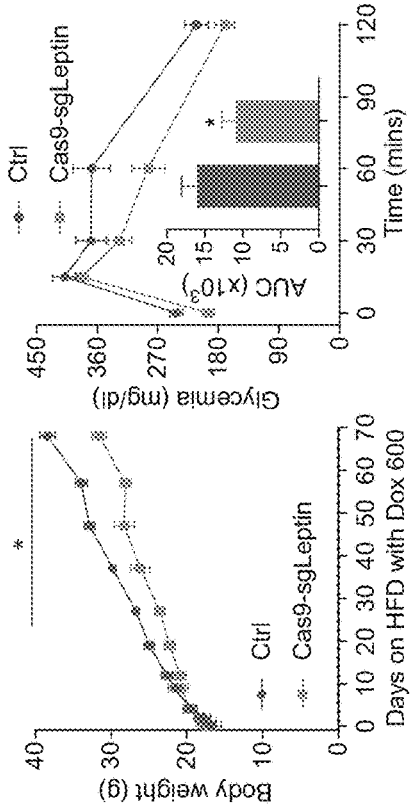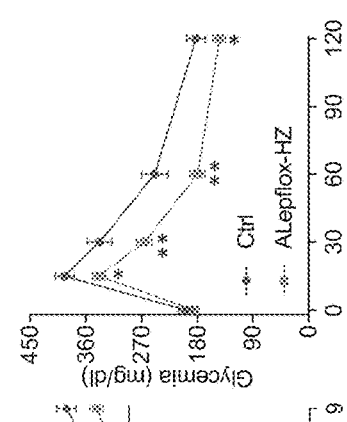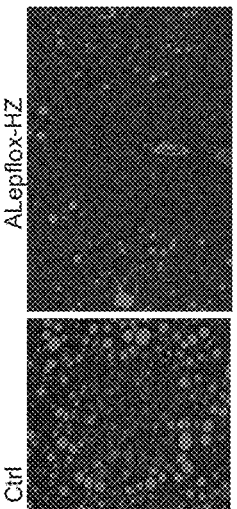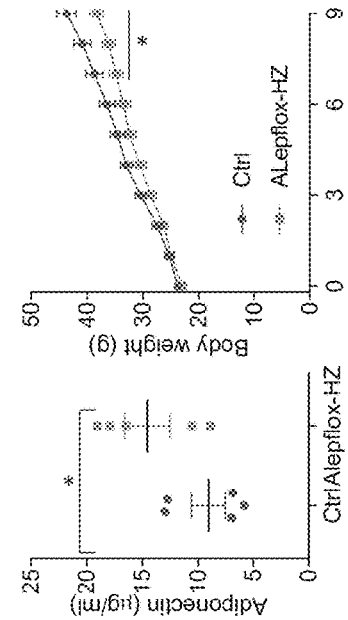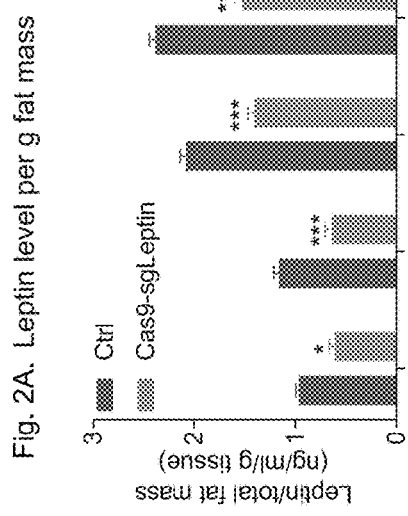

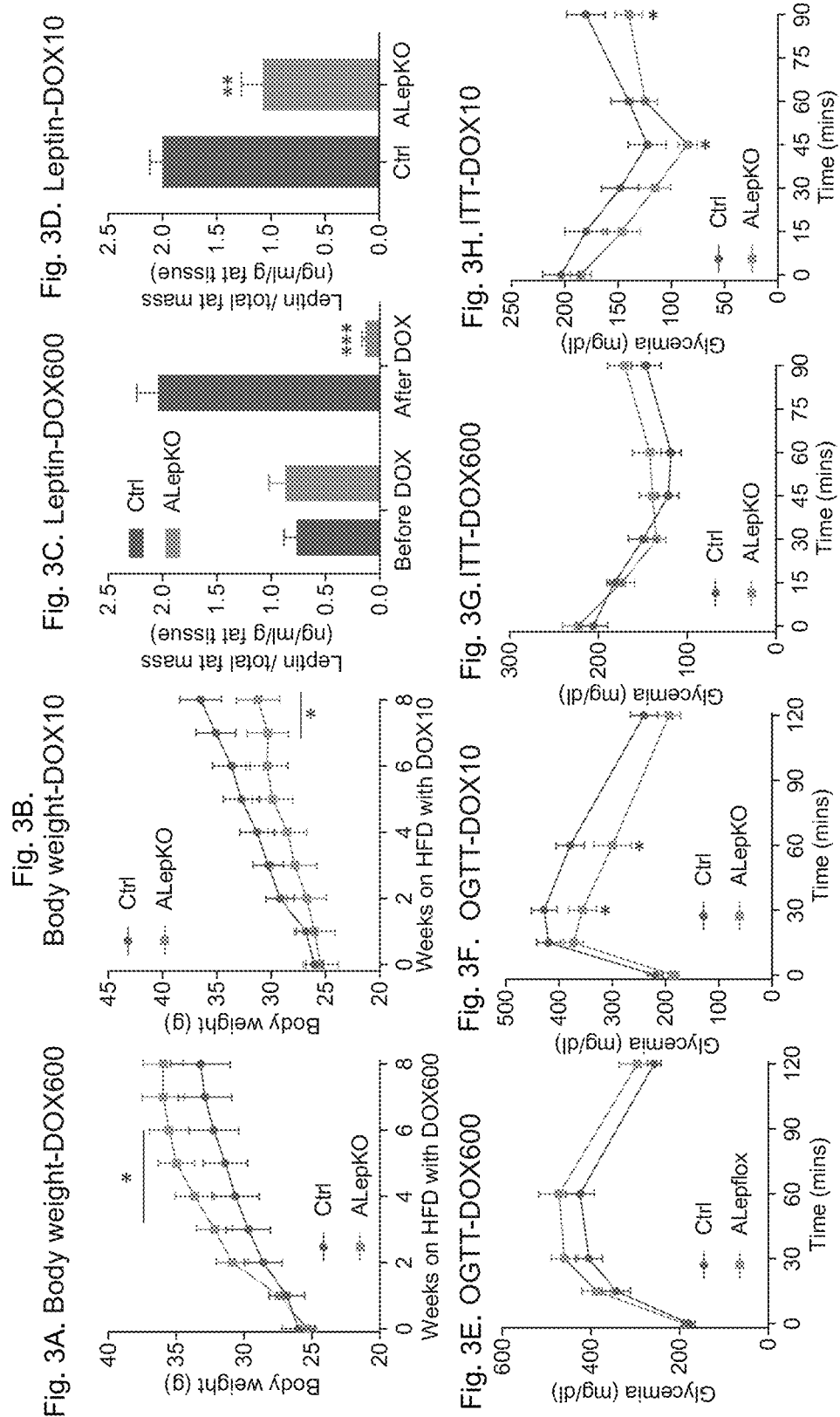

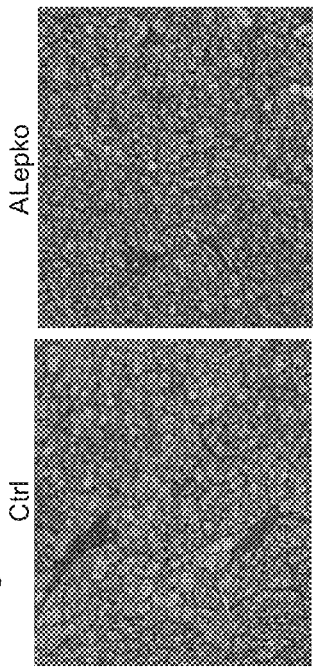
Fig. 3J. Histology of brown fat-DOX10
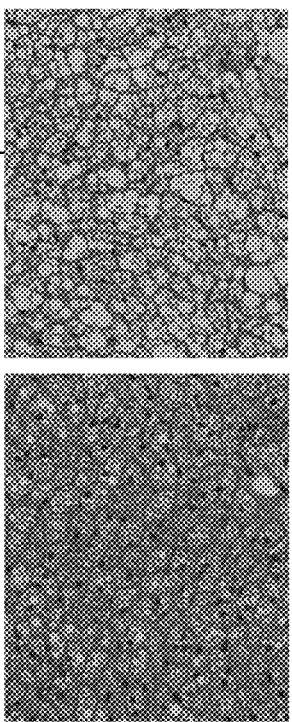
Fig. 3I. Histology of brown fat-DOX600
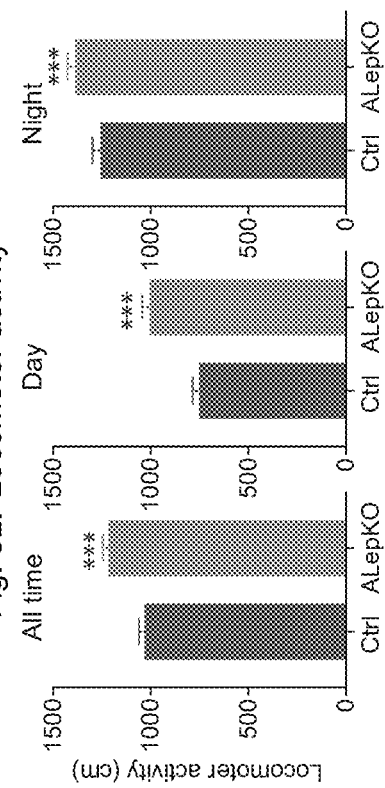
Fig. 3K. VO₂
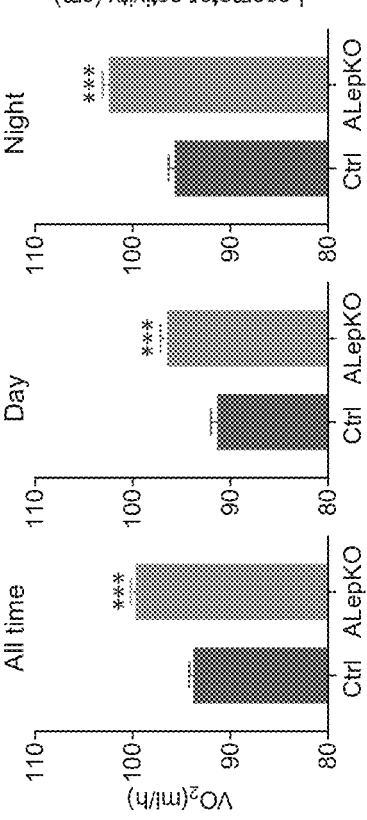
Fig. 3L. Locomotor activity

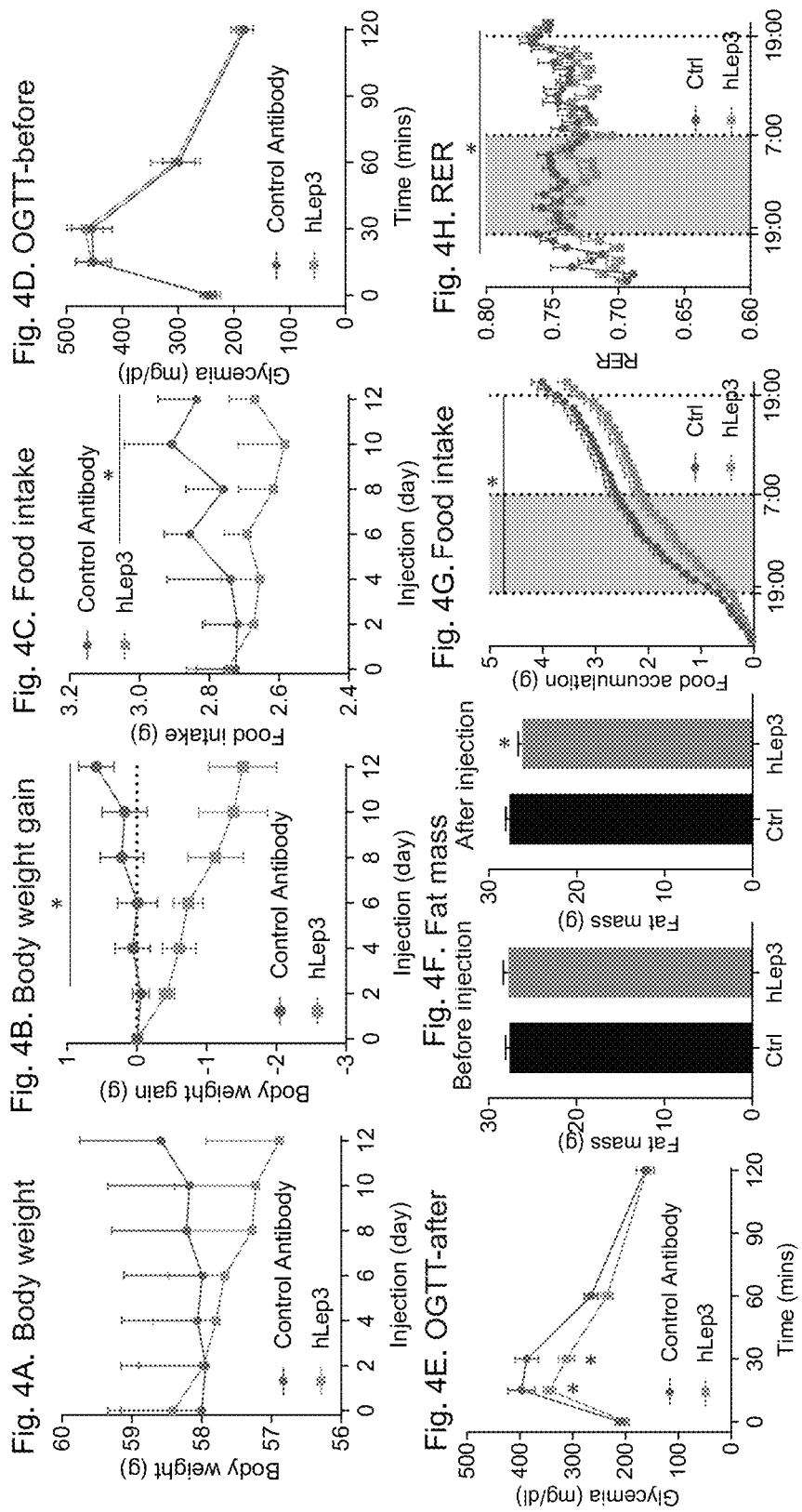

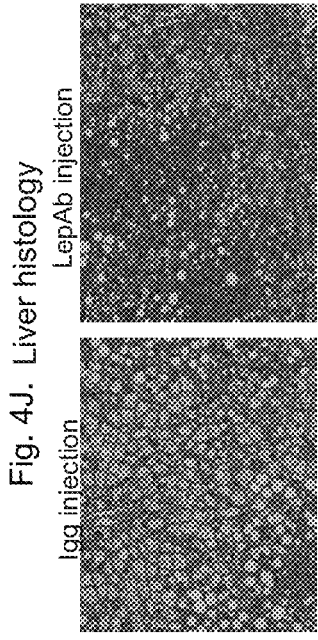
Fig. 4I. Histology of brown fat
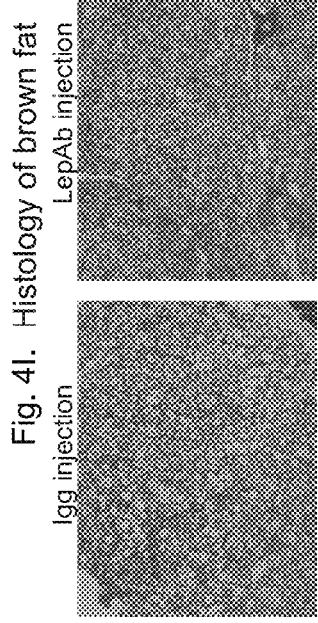
Fig. 4J. Liver histology
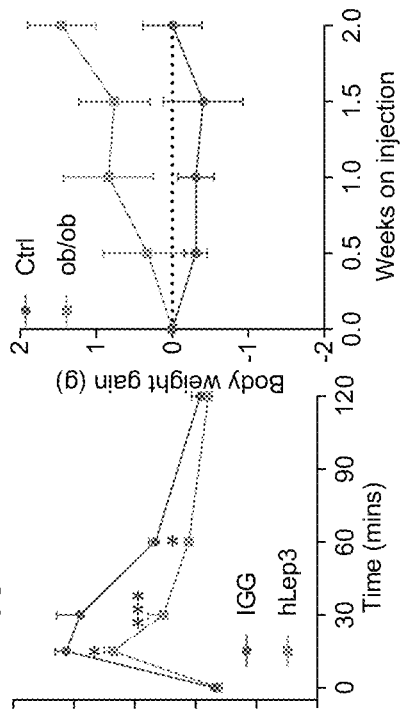
Fig. 4K. Injection in thermal conditions
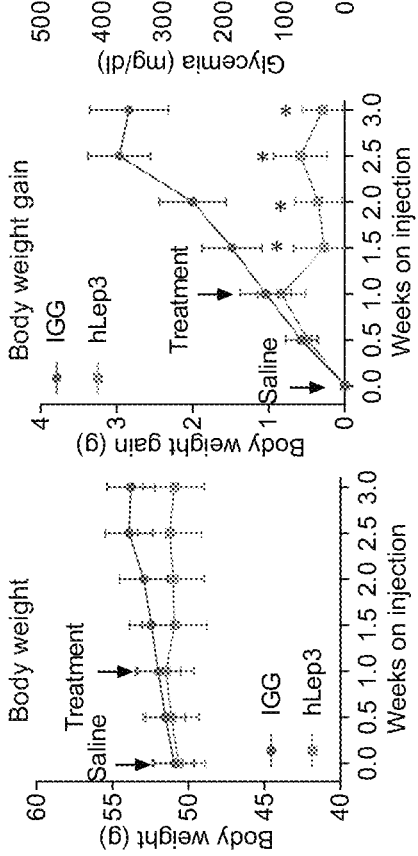
Fig. 4L. Inducible ob/ob

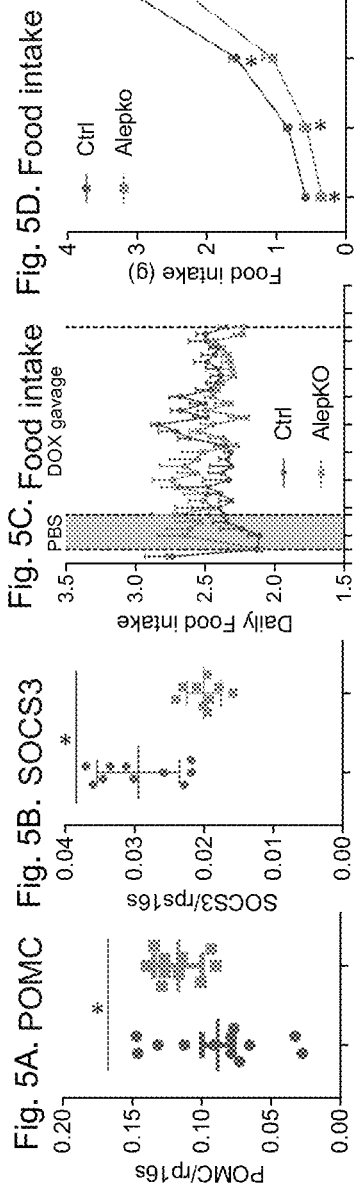
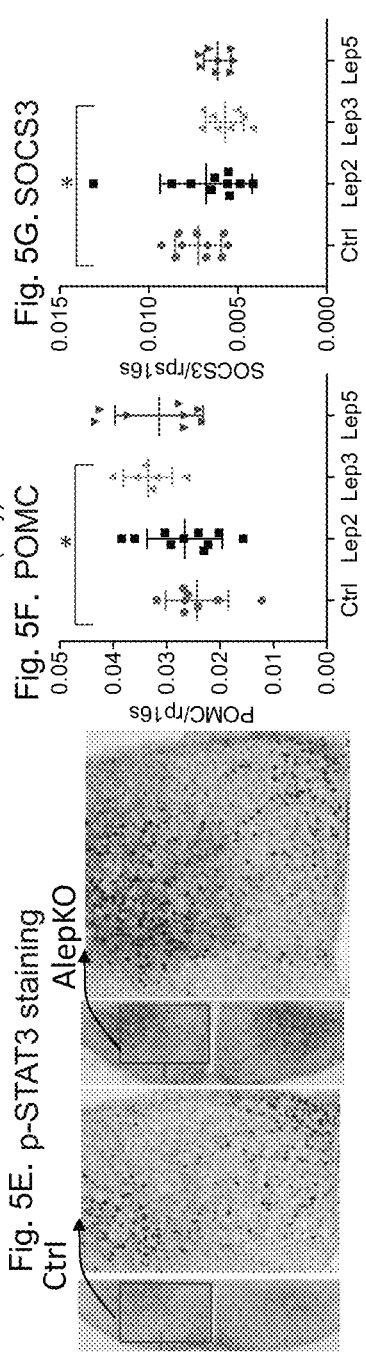
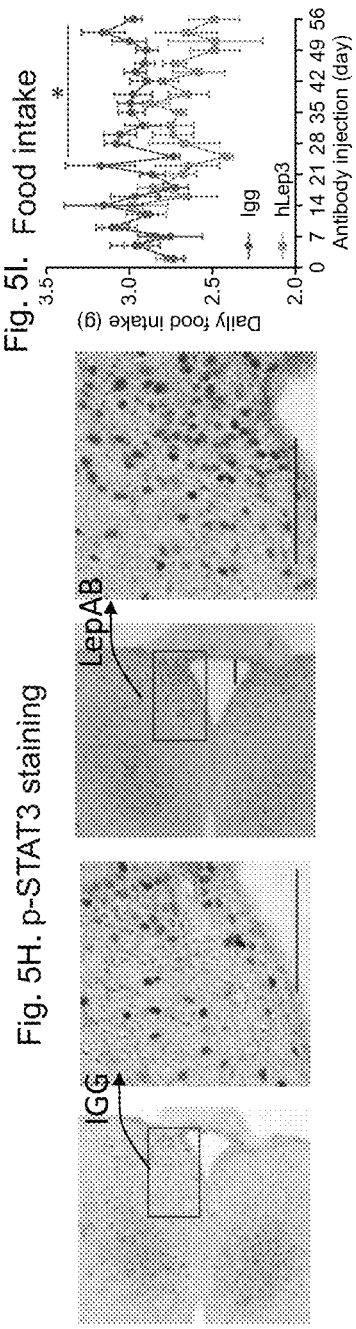

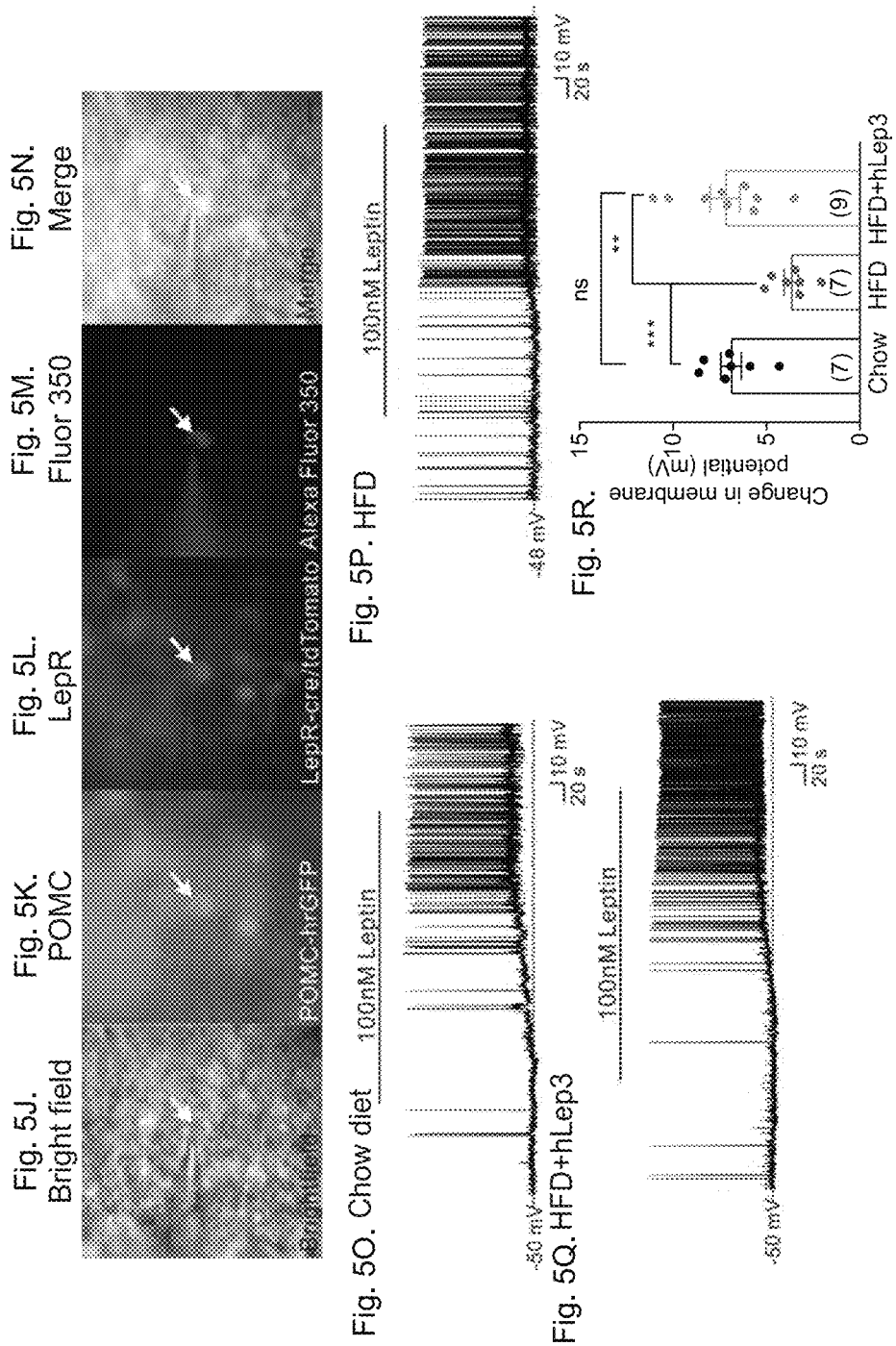

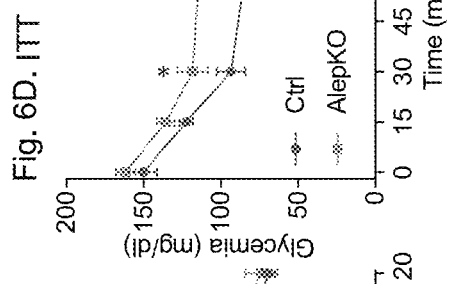
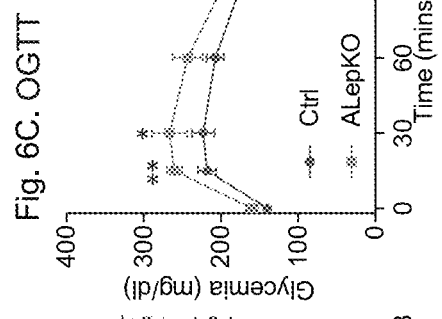
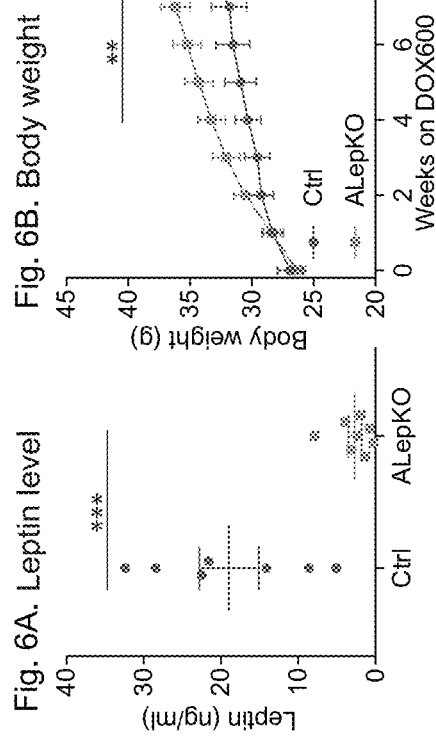
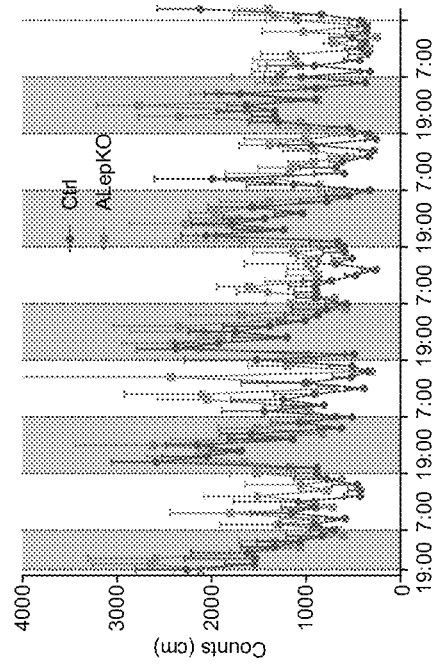
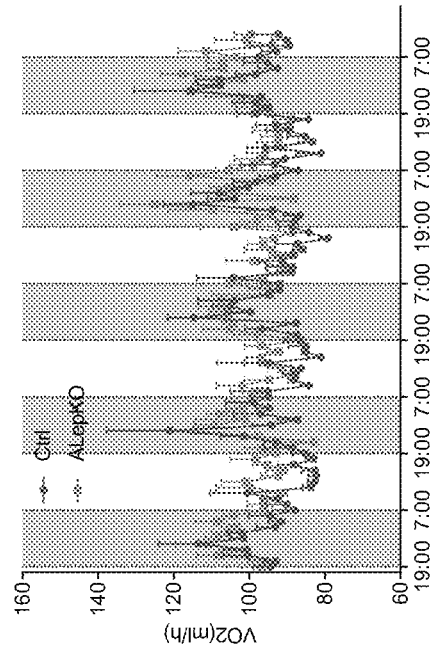

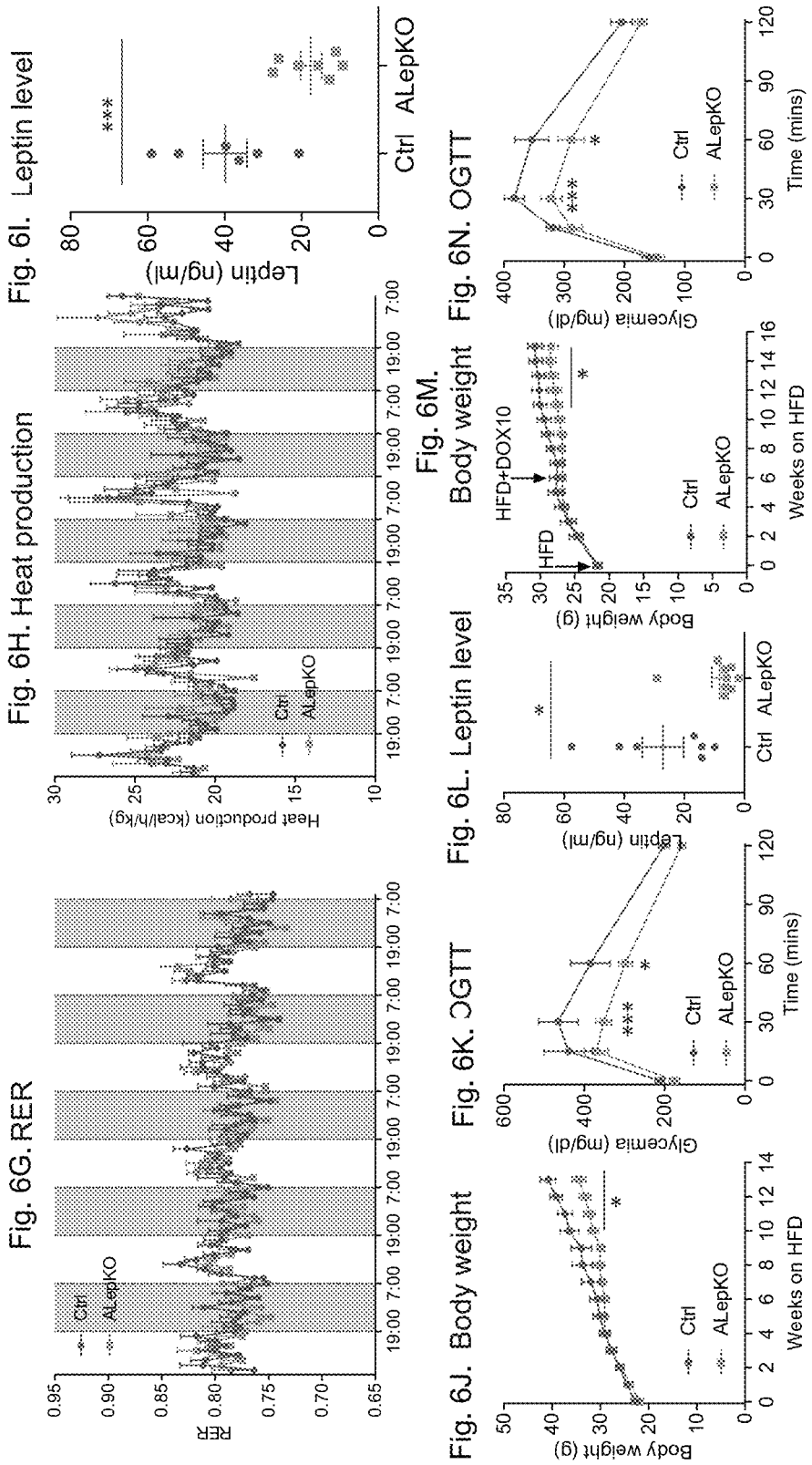

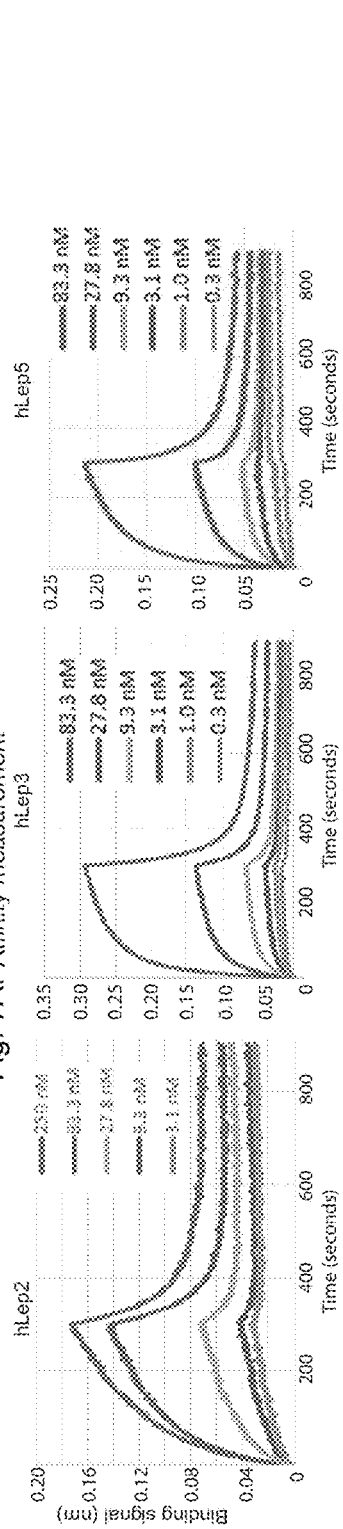
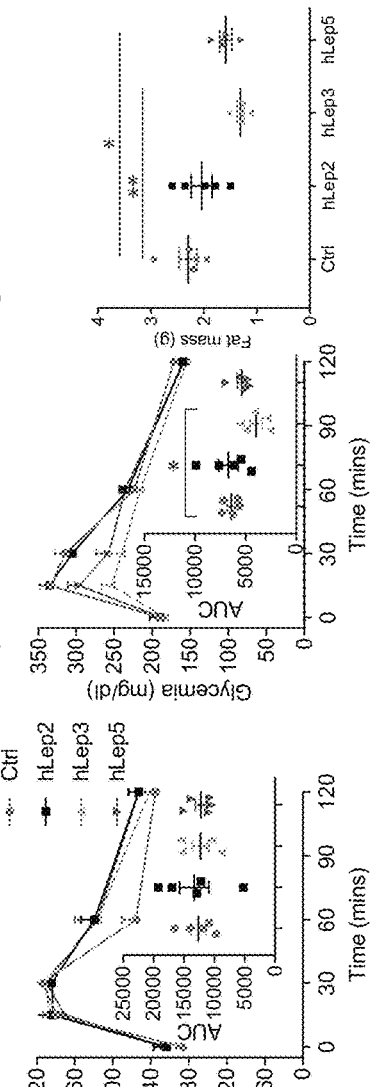
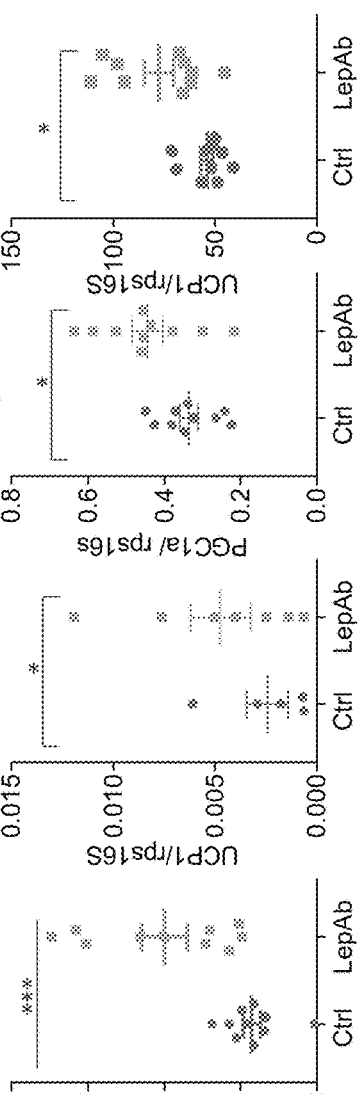
Fig. 7A. Affinity measurement
Fig. 7B. Body weight gain
Fig. 7C. OGTT-before injection
Fig. 7D. OGTT-after injection
Fig. 7E. Gonadal fat
Fig. 7F. Leptin level
Fig. 7G. Epididymal fat
Fig. 7H. Brown fat

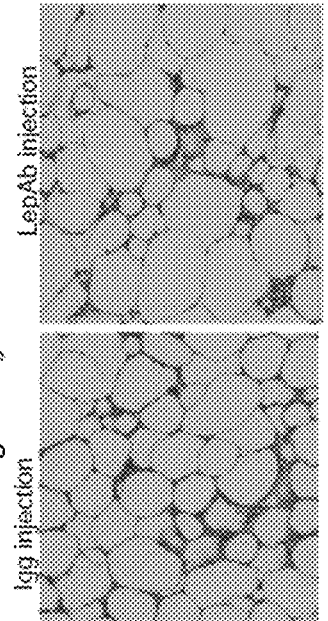
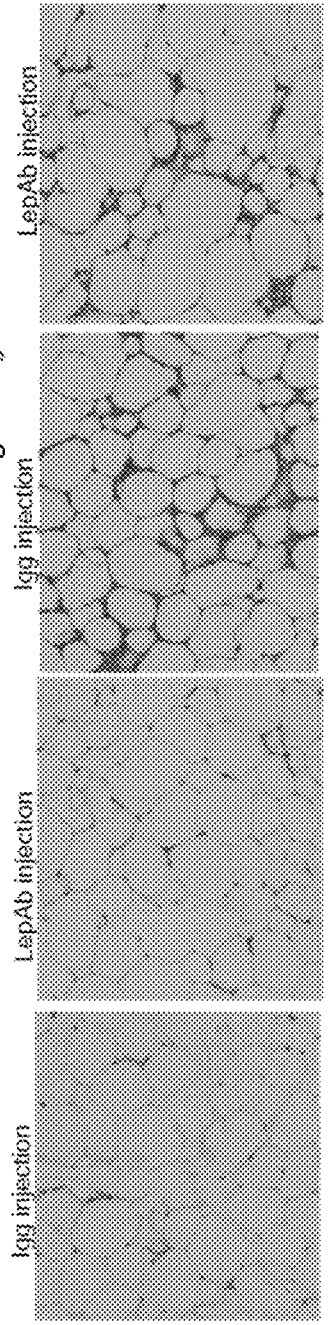
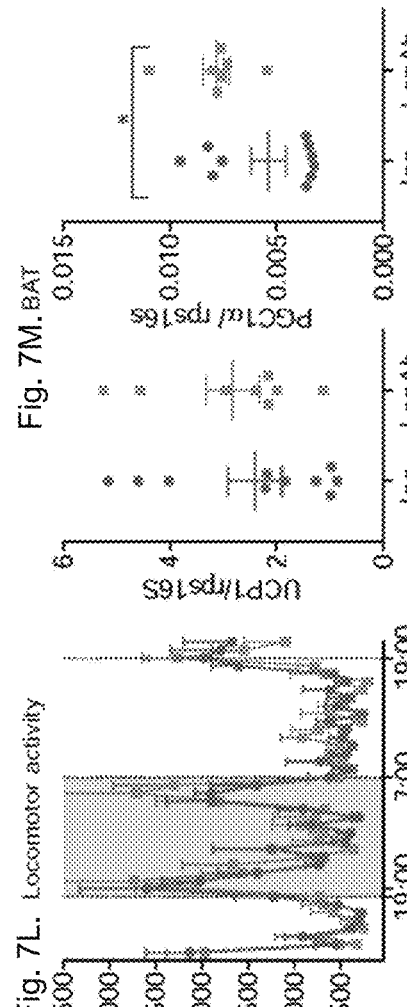
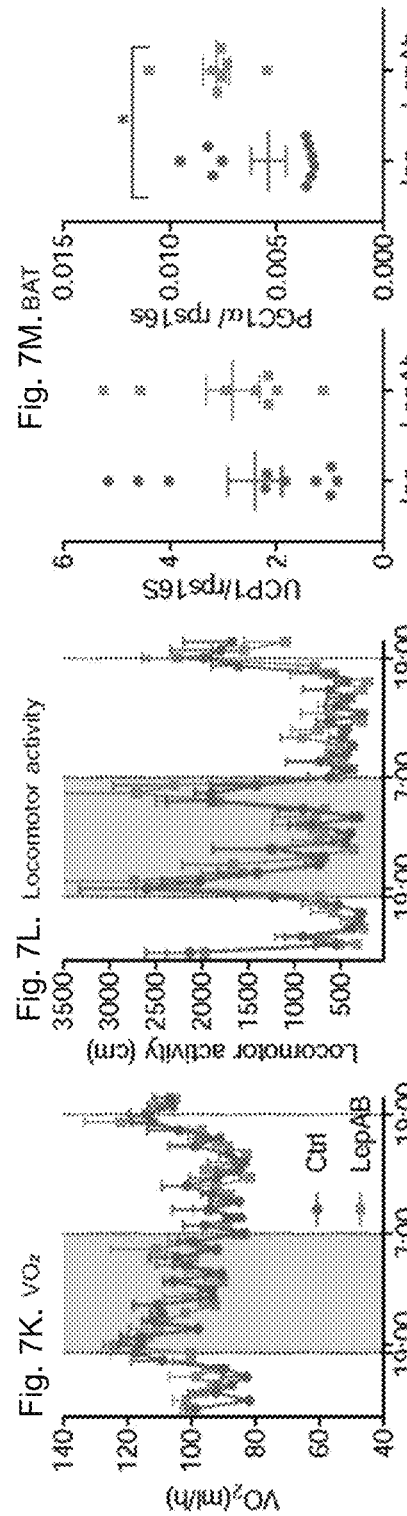
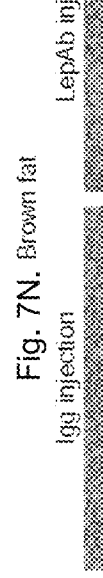
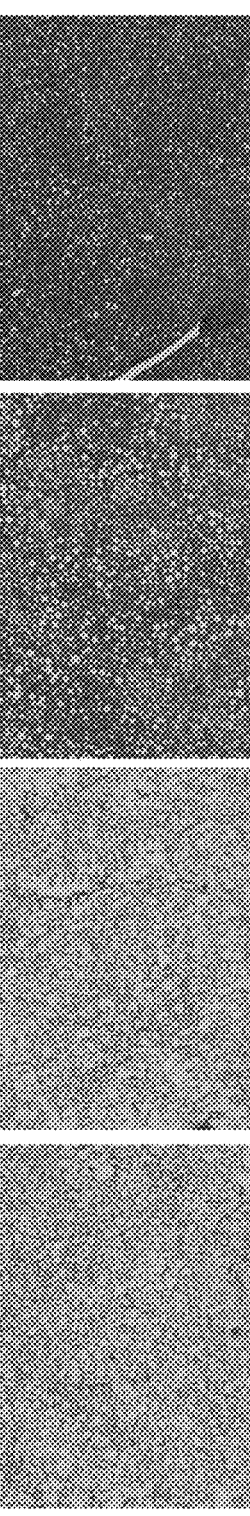

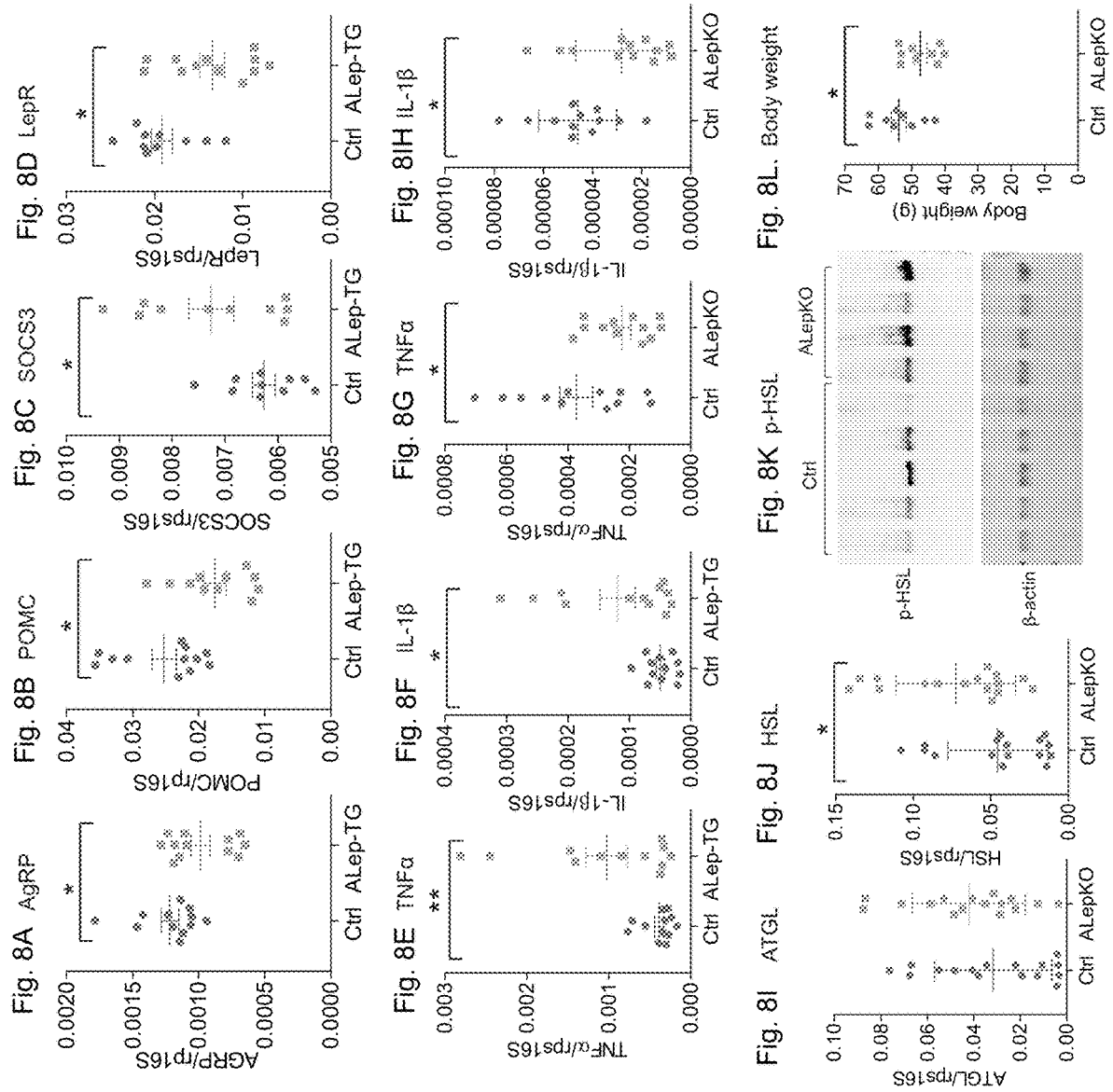

WEIGHT LOSS REGIMEN

INTRODUCTION

Obesity remains one of the most prominent risk factors for a large number of chronic diseases, including diabetes, cardiovascular disease, fatty liver disease and most types of cancer (Scherer, 2016). Despite life-style and surgical interventions, and some limited pharmacological therapies, there remains an unmet need to promote and sustain significant weight loss in overweight and obese individuals (Kusminski et al., 2016). The inefficacy of homeostatic weight control in the context of obesity remains one of the largest global public health issues.

As one of the first adipokines identified, hopes were extremely high that leptin could reduce food-intake and promote energy expenditure (Friedman and Halaas, 1998). Congenital loss of leptin results in severe obesity in both rodents and humans (Montague et al., 1997). Administration of recombinant leptin provides an effective means to reduce obesity in leptin-deficient individuals (Farooqi et al., 1999). Furthermore, extremely low levels of leptin, evident in lipodystrophic patients, can be corrected using exogenous leptin treatment, which dramatically improves lipid and carbohydrate metabolism (Shimomura et al., 1999). However, injecting additional leptin, in the context of conventional obesity, is largely ineffective. Obese individuals do not lack leptin, rather they display higher circulating levels of leptin, and these elevated levels are associated with leptin resistance and impaired leptin signaling in the brain (Zelissen et al., 2005). Leptin "resistance" is therefore defined as the inability of elevated leptin levels (either endogenous or pharmacologically administered) to reduce food intake and cause weight loss (Ahima and Flier, 2000; Flier and Maratos-Flier, 2017; Friedman, 2016). However, there is also the concept of "selective leptin resistance" (Mark, 2013), whereby not all leptin signaling pathways are equally affected. While the complete lack of leptin signaling can cause infertility, not all obese individuals are infertile since some leptin signaling is preserved both centrally as well as peripherally (Hausman et al., 2012).

Hyperleptinemia is necessary and sufficient to induce leptin resistance in wild-type mice (Knight et al., 2010), as well as in leptin super-sensitive ob/ob mice upon chronic leptin injection (Koch et al., 2014). In contrast, congenital elevation of leptin leading to a "transgenic skinny" mouse resulted in increased glucose metabolism and insulin sensitivity (Ogawa et al., 2002). Similarly, chronic infusions of leptin intracerebroventricularly (i.c.v.) at doses of 3 ng/hr or greater resulted in complete depletion of visible adipose tissue, which was maintained throughout 30 days of continuous i.c.v. infusion (Halaas et al., 1997). So the mechanisms of leptin resistance are still poorly understood (Flier and Maratos-Flier, 2017).

Developmentally, leptin plays a critical role in the generation of the neuronal circuitry (Zeltser, 2015). While the congenital loss of leptin results in severe obesity, to date, no attempts have been made to achieve a reduction in leptin levels only in the adult stage, while leaving the remaining adipose tissue depots intact and functional.

Here, based on distinct genetic approaches and an independent antibody-based approach, we report a series of novel and unique observations, in which a decremental reduction in circulating leptin levels initiates an unexpected and significant improvement in several parameters of energy balance and glucose homeostasis. This system-wide response includes significant weight loss, reduced food-intake and increased energy expenditure; all indicative of enhanced leptin sensitization.

There are prior suggestions of targeting leptin and/or leptin receptor to treat cancer (e.g. Pierre V Candelaria et al. World J Clin Oncol. 2017 Apr. 10; 8(2): 106-119; Zheng, et al. Biology Open 2016; Higurashi et al. Carcinogenesis. 2014 September; 35(9):2134-41), arterial and venous thrombosis (Konstantinides et al, Arteriosclerosis, Thrombosis, and Vascular Biology. 2004; 24:2196-2201) and rheumatoid arthritis (e.g. Tian, et al, Clin Exp Immunol. 2014 September; 177(3): 557-570).

SUMMARY OF THE INVENTION

The invention provides methods and compositions for treating obesity and/or diabetes. In an aspect the invention provides a method of treating obesity or diabetes comprising partially inhibiting circulating leptin by 30-90% in a person in need thereof.

In embodiments:
the partial inhibition is about 40-80%, or about 50-70%;
the inhibiting step comprises administering to the person a therapeutic leptin neutralizing antibody;
the inhibiting step comprises administering to the person a therapeutic leptin neutralizing antibody, wherein the antibody neutralizes by reducing engagement of leptin receptor and subsequent signaling of the receptor as assessed by STAT activation, wherein circulating leptin is reduced, and in embodiments, this reduction results in sensitization to the lower leptin levels, i.e. the lower circulating levels result in an increase in receptor signaling;
the inhibiting step comprises administering to the person a therapeutic leptin antagonist, such as a leptin mutein, such as Lan1 (L39A/D40A/F41A mutant), Lan2 (L39A/D40A/F41A/142A mutant) and SHLA (D23L/L39A/D40A/F41A mutant;
the inhibiting step comprises administering to the person a therapeutic leptin neutralizing antisense oligonucleotide (ASO), small interfering RNA (siRNAs) or short hairpin RNA (shRNA);
inhibiting step comprises knocking down of leptin expression using CRISPR/Cas9 or CRE/loxP;
the method further comprises detecting a resultant improvement in the obesity or diabetes in the person;
detecting a resultant partial inhibition of circulating leptin in the person; and/or
titrating down the levels of leptin of the person to effect leptin sensitization without effecting weight gain; such as:
administering a therapeutic leptin neutralizing antibody, detecting a resultant change in circulating leptin in the person, and administering a therapeutic leptin neutralizing antibody to titrate down the levels of leptin of the person to partially inhibiting circulating leptin by 30-90%, or 40-80%, to effect leptin sensitization without effecting weight gain;

The invention includes all combinations of the recited particular embodiments as if each combination had been laboriously separately recited.

BRIEF DESCRIPTION OF THE DRAWINGS

FIGS. 1(A)-1(M): Increasing leptin levels in obese mice exacerbates obesity and metabolic dysfunction. Leptin gene expression from various fat depots collected from wildtype (WT) mice transferred from a chow diet to a HFD (A). Circulating leptin levels in WT mice from chow diet to HFD (B); ALep-TG and littermate control mice at 8-weeks of age were placed on HFD for 6 weeks and then switched to HFD diet with Dox (600 mg/kg). Leptin (C), insulin (D) and adiponectin (E) levels were measured before and after supplementing DOX in the diet, and leptin level was normalized by total fat mass. Body weight gain (F), fat mass (G), lean mass (H), oral glucose tolerance tests (OGTT) before (I) and after (J) DOX diet as well as insulin tolerance tests (ITT) (K) after DOX were done in ALep-TG and littermate Ctrl mice. Histology of HE staining of liver (L) and brown fat (M) were assessed after euthanizing the mice.

FIGS. 2(A)-2(I): Partial leptin reduction in mice protects against diet-induced obesity. Cas9-sgLeptin and littermate control mice at age of 8-week old were placed in HFD with Dox 600 for 10 weeks. (A) Circulating leptin levels per total fat mass in Cas9-sgLeptin and littermate control mice at the indicated time points; (B) body weight gain during HFD feeding in Cas9-sgLeptin and littermate control mice. (C) OGTT on Cas9-sgLeptin and control mice. Area under curve (AUC) was calculated and inserted inside this figure; Alepflox-HZ and littermate control mice at 8-weeks of age were placed in HFD with Dox 600 for 9 weeks. Two different cohorts of mice were used in this study. circulating leptin (D) and adiponectin (E) levels measured in the first cohort of Alepflox-HZ and control mice; (F) body weight gain in ALepflox-HZ and control mice; (G) OGTT in ALepflox-HZ and control mice. After euthanizing the mice, brown fat (H) and liver (I) were processed for H&E staining.

FIGS. 3(A)-3(L): Partial, not complete reduction of circulating leptin, protects mice from obesity. ALepKO and littermate control mice were placed on HFD supplemented with two different amounts of Doxycycline (DOX) (600 mg/kg (DOX600) and 10 mg/kg (DOX10)). Body weight, circulating leptin levels, OGTT, ITT and histology were performed. (A) Body weight gain of ALepKO and littermate controls on DOX600; (B) body weight gain ALepKO and littermate controls on DOX10; (C) Circulating leptin levels per total fat mass of ALepKO and littermate controls before and after DOX 600; (D) Circulating leptin per total fat mass of ALepKO and littermate controls on DOX10; (E) OGTT on ALepKO and littermate controls on DOX600; (F) OGTT on ALepKO and littermate controls on DOX10; (G) ITT on ALepKO and littermate controls DOX600; (H) ITT on ALepKO and littermate controls on DOX 10; (I) Brown adipose tissue histology on DOX600; (J) Brown adipose tissue histology on DOX10; (K) Oxygen consumption ($VO_2$) of ALepKO and littermate controls on DOX10 in metabolic cages; (L) Locomotor activity of ALepKO mice and littermate controls on DOX10 during the dark period, daytime and across the entire 24 hr period.

FIGS. 4(A)-4(L): Decreasing leptin levels with neutralizing anti-leptin antibodies reduces body weight gain and liver steatosis. A cohort of obese mice were treated either with control antibody or leptin neutralizing antibody (hLep3) for two weeks. Antibody injection was done every other day. Body weight (A) and food intake (C) were measured before each injection. Body weight gain was calculated (B); OGTT was performed before (D) and (E) after antibody injection; Total fat mass (F) was measured by Eco-MRI. For the metabolic cage study, obese WT mice were treated with a control antibody (hIGG) or hLep3 antibody. (G) Food accumulation measured in metabolic cages after vehicle or hLep3 treatment; (H) RER measured in vehicle and hLep3 treated mice; After a two-week treatment period, mice were euthanized and brown fat and liver were collected for histology analysis. H&E staining of brown adipose tissue (I) and liver (J); Obese WT mice were housed in thermal neutral chambers and treated with control antibody (hIGG) or hLep3 neutralizing antibody for two weeks (K) Effects of the neutralizing antibody hLep3 on body weight, body weight gain and OGTT on mice housed in thermal chambers; (L) Effect of hLep3 on body weight gain in inducible ob/ob mice.

FIGS. 5(A)-5(R): Leptin sensitivity is inversely correlated with circulating leptin levels. Expression of pomc (A) and socs3 (B) in ARH region of control and AlepKO mice; (C) Daily food intake was measured in control and ALepKO mice during PBS and a low dose Doxycycline (5 mg/kg body weight) oral gavage period; (D) Effects of acute leptin injection on food intake in ALepKO and littermate control mice after overnight fasting; (E) DAB staining of p-STAT3 after leptin injection in ALepKO and Ctrl mice; (F) Gene expression of pomc in ARH region after neutralizing leptin antibody treatment. (G) Gene expression of socs3 in ARH region after neutralizing leptin antibody treatment. (H) DAB staining of p-STAT3 after leptin injection in neutralizing hLEP3 treated mice; (I) Effects on food intake in obese WT mice (vehicle vs mLep3) were chronically treated with control antibody (mIGG) or a mouse version of the neutralizing leptin antibody (mLep3); (J-N) Brightfield illumination (J) of a POMC neuron that expresses leptin receptors from POMC-hrGFP::LepR-cre:adtomato mice. (K) and (L) show the same neuron under FITC (hrGFP, green cell) and Alexa Fluor 594 (tdtomato, red cell) illumination. Complete dialysis of Alexa Fluor 350 from the intracellular pipette is shown in (M) and a merged image of a POMC neuron targeted for electrophysiological recording (N). Merged image. (Arrow indicates the targeted cell. Scale bar=50 µm). (O) Representative electrophysiological trace demonstrating a Leptin receptor expressing POMC neuron from chow diet-fed mice is depolarized by leptin (100 nM). (P) Representative electrophysiological trace demonstrating a leptin receptor expressing POMC neuron from HFD feeding mice is depolarized by leptin (100 nM). (Q) Representative electrophysiological trace demonstrating a Leptin receptor expressing POMC neuron from HFD feeding mice which is injected with neutralizing antibody is depolarized by leptin (100 nM). (R) Histogram illustrates the acute effects of leptin (100 nM) on the membrane potential of leptin receptor expressing POMC neurons from chow or HFD feeding mice with or without antibody injection.

FIGS. 6(A)-6(N): Partial reduction of leptin slows down body weight gain and improves glucose tolerance. A cohort of AlepKO mice and littermate control mice were placed on chow diet with DOX600 for various time points, as indicated in the figures, leptin levels (A), body weight (B), OGTT (C) and ITT (D) were measured after 8 weeks. A cohort of AlepKO mice and littermate control mice were placed into metabolic cages. Various parameters were measured. (E) traces of $O_2$ consumption and (F) locomotor activity, (G) RER and (H) heat production; A cohort of AlepKO mice and littermate control mice were placed on chow diet with DOX600 for one week to induce some levels of leptin deletion, and then switched to HFD without Dox for different time. During HFD period, body weight (J) was taken on a weekly basis and OGTT (K) and leptin levels (I) were done after 8-weeks on HFD. A cohort of AlepKO mice and littermate control mice were placed on HFD diet for 5 weeks and then switched to HFD plus DOX10 for another 8 weeks. Circulating leptin levels (L), body weight (M) and OGTT (N) were measured after 8 weeks with DOX10.

FIGS. 7(A)-7(O): (A) In vitro cell based assay for characterizing of three hLep neutralizing antibodies; Obese WT mice were treated with vehicle or three different human leptin neutralizing antibodies for two weeks. (B) Effects of three different neutralizing antibodies (hLep2, hLep3 and hLep5) on body weight gain. OGTT before (C) and after (D) treatment with three different neutralizing antibodies; (E) Weight of epididymal adipose tissue after neutralizing antibody treatment; (F) free leptin levels after neutralizing antibody treatment; PGC1α and UCP1 expression in inguinal (G) and brown fat (H); Histology of subQ (I) and epididymal fat (J) after neutralizing antibody treatment; Tracers of $O_2$ consumption (K) and locomotor activity (L) after neutralizing antibody treatment; A cohort of obese WT mice were housed in thermal chambers, and treated with control antibody (hIGG) and hLep3 antibody for 2 weeks. Then the mice were euthanized and tissues were collected for gene expression and histology. UCP1 and PGC1α expression (M) in brown fat were measured by RT-PCR. H&E staining of brown fat (N) and liver (O) under thermoneutral housing.

FIGS. 8(A)-8(L): Partial reduction of leptin ameliorates MBH inflammation and increases adipose tissue leptin sensitivity. Expression levels of agrp (A), pomc (B), socs3 (C), lepr (D), tnfα (E) and il-1β (F) in ALep-TG and littermate Ctrl mice. TNFα (G) and IL-1β (H) in Ctrl and AlepKO mice; Expression of atgl (I) and hsl (J) in gonadal fat in AlepKO mice and littermate controls on HFD with dox 10; (K) p-HSL level in gonadal fat of AlepKO and littermate control mice on HFD with DOX10. (L) Body weights of control and AlepKO mice after 8 months on HFD with Dox 10.

DESCRIPTION OF PARTICULAR EMBODIMENTS OF THE INVENTION

We disclose that a range of partial reduction of circulating leptin levels in the obese state prompts an entirely unexpected systemic response resulting in weight loss, reduced food intake and increased energy expenditure, consistent with leptin sensitization in central neurons. While a higher or complete loss of leptin triggers increased obesity, and a lower loss is ineffective under thermoneutral conditions, this partial reduction prompts weight loss. We confirmed this by two distinct genetic approaches as well as a third independent, antibody-based approach, and in each case, we confirmed that the partial leptin reduction leads to metabolic improvements. In contrast to the central leptin action (or lack thereof) in the hypothalamus, the peripheral leptin effects do not show any signs of leptin resistance. Here we disclose that partial reduction of leptin (e.g. by neutralizing antibodies, Crisper/Cas9-based technologies, shRNA, etc) leads to leptin sensitization and weight loss and improvements in insulin sensitivity.

There is widespread expression of various leptin receptor isoforms in the periphery. We also demonstrated a dramatic upregulation of the leptin receptor in the context of breast cancer cells. The leptin signaling pathway is operative in breast cancer cells, and we have shown that tumor lesions lacking the leptin receptor show a dramatically reduced growth rate. Here we disclose that partial reduction of leptin in the context of breast cancer and other cancers results in a reduction in tumor growth.

The invention provides antibodies which neutralize leptin by reducing engagement of leptin receptor and subsequent signaling of the receptor as assessed by STAT activation, wherein circulating leptin is reduced.

Unless the context indicates otherwise, the term "antibody" is used in the broadest sense and specifically covers antibodies (including full length monoclonal antibodies) and antibody fragments so long as they neutralize leptin. An antibody molecule is usually monospecific, but may also be described as idiospecific, heterospecific, or polyspecific. Antibody molecules bind by means of specific binding sites to specific antigenic determinants or epitopes on antigens. "Antibody fragments" comprise a portion of a full length antibody, generally the antigen binding or variable region thereof. Examples of antibody fragments include Fab, Fab', F(ab').sub.2, and Fv fragments; diabodies; linear antibodies; single-chain antibody molecules; and multispecific antibodies formed from antibody fragments.

Natural and engineered antibody structures are well known in the art, e.g. Strohl et al., *Therapeutic antibody engineering: Current and future advances driving the strongest growth area in the pharmaceutical industry*, Woodhead Publishing Series in Biomedicine No. 11, October 2012; Holliger et al. Nature Biotechnol 23, 1126-1136 (2005); Chames et al. Br J Pharmacol. 2009 May; 157(2): 220-233.

Monoclonal antibodies (MAbs) may be obtained by methods known to those skilled in the art. See, for example Kohler et al (1975); U.S. Pat. No. 4,376,110; Ausubel et al (1987-1999); Harlow et al (1988); and Colligan et al (1993). The mAbs of the invention may be of any immunoglobulin class including IgG, IgM, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Preferred antibodies are humanized to a high degree of similarity to human antibodies in the framework regions to facilitate therapeutic use in humans.

Suitable leptin neutralizing antibodies are commercially available and/or readily produced as disclosed herein.

EXAMPLES

Partial Leptin Reduction as an Effective Weight Loss Strategy: Increasing Leptin Levels in Obese Mice Enhances Body Weight Gain The leptin gene expression and circulating leptin level are tightly regulated under most physiological conditions. Here, we show that acute high fat diet (HFD) feeding of wild-type (WT) mice significantly upregulates leptin expression in gWAT, with a lesser induction evident for sWAT and brown adipose tissue (BAT) (FIG. 1A). Consistent with these observations, short-term HFD feeding dramatically increases the circulating levels of leptin (FIG. 1B).

To further define the physiological roles of leptin, we generated an inducible adipocyte-specific leptin transgenic mouse (Alep-TG). We fed lean Alep-TG and littermate control mice with chow-diet supplemented with Dox600 (600 mg/kg Dox) for 1 week and observed that leptin expression is significantly induced in sWAT, gWAT and BAT depots; with no induction evident in the liver in Alep-TG mice compared to control mice. Importantly, no significant differences were observed for adiponectin and for other key genes (such as TNFα and ATGL) in the different fat-depots with acute leptin induction; confirming that our transgenic mouse model is specific to leptin. Upon Dox supplementation in mice on chow diet, the circulating levels of leptin are significantly increased in Alep-TG, by approximately 3-fold compared to control mice, without a significant change in adiponectin levels.

To assess the role of leptin in the context of obesity, Alep-TG and Ctrl mice were fed a HFD for 6-weeks to induce obesity and insulin resistance. Prior to induction, circulating levels of leptin per total fat mass are similar between ctrl and Alep-TG groups (FIG. 1C). Transgenic leptin was then induced by adding DOX600 to the HFD to both groups. Following induction with DOX for 6 weeks, Alep-TG mice display a significant increase in circulating leptin levels (FIG. 1C). Interestingly, in parallel with this increase in leptin, insulin levels are also doubled (FIG. 1D) and adiponectin levels are decreased (FIG. 1E). Prior to leptin gene induction, there is no difference in body weight and glucose tolerance between Ctrl and Alep-TG mice (FIGS. 1F and I). Upon transgene induction with Dox, we observe that the higher leptin levels in Alep-TG trigger accelerated body weight gain (FIG. 1F) with significantly increases in fat mass (FIG. 1G), but not in lean mass (FIG. 1H), concomitant with impaired glucose tolerance and insulin sensitivity (FIG. 1J-K). After switching diet from HFD only to HFD with DOX600, it seems that ALep-TG and Ctrl mice reduce their rate of body weight gain, and this may be due to reduced intake of new diet. As Alep-TG and Ctrl mice were placed on the same diet all the time, it will not introduce extra artifacts in this study. Alep-TG mice display enhanced hepatic steatosis with an associated "whitening" of BAT; the latter frequently associated with a reduction in brown-fat function (Kusminski et al., 2014; Zhu et al., 2016)(FIG. 1L-M). Taken together, these results indicate that solely on the basis of increasing the leptin levels in the obese state, without altering adipose tissue in any other way during the onset of the leptin increase, greatly exacerbates metabolic dysfunction. This indicates that enhancing leptin levels per se in the obese state is sufficient to trigger pathological changes.

A Cas9/Crisper-Based Approach for Inducible Elimination of Leptin Specifically from the Mature Adipocyte In light of the fact that high leptin is sufficient to induce leptin resistance and trigger pathological changes, we wondered what would occur if leptin levels are reduced in the setting of obesity at the adult stage. In order to do this, we generated Cas9-sgLeptin mice, a strain that enables us to do a doxycycline-inducible elimination of leptin in the adipose tissues of adult mice. As expected, within as little as 2 days of Dox-HFD feeding, Cas9-sgLeptin mice exhibit a significant decrease in circulating leptin levels per total fat mass (FIG. 2A), and this leptin reduction is well-maintained up to 8 weeks (FIG. 2A). In addition, Cas9-sgLeptin mice display a marked reduction in body weight gain (FIG. 2B). This is an entirely unexpected finding, since we assumed that a reduction in leptin would prompt increased weight gain, as typically observed with a congenital leptin deficiency in the ob/ob mouse (Nunziata et al., 2019). Measurements of plasma leptin concentrations reveal that the system is not particularly effective, since the circulating levels of leptin are reduced by only about 50%, when compared with Dox-treated littermate control mice (FIG. 2A). We consistently observed the association between lowering leptin and reduced body weight gain over multiple cohorts, along with improvements in oral glucose tolerance (FIG. 2C). However, since the response is unexpected and is in direct contrast to the prior observations made using heterozygous ob$^+$ mice, we decided to validate the observed effects with additional, independent approaches.

Genetic Elimination of Leptin in the Adult Mouse Using a Classical Cre-loxP System To confirm these observations, we employed a classical Cre-loxP approach for leptin elimination. In order to achieve a situation similar to the Cas9/Crisper-based approach and also to be able to compare the phenotype with the heterozygous ob$^+$ mice, in which partial leptin deficiency favors diet-induced obesity and unfavorable metabolic phenotypes (Begriche et al., 2008), we began utilizing ALepflox-HZ mice, in which we eliminate only one copy of the leptin gene at the adult stage. As expected, the circulating levels of leptin levels are reduced by approximately 50% in ALepflox-HZ mice (FIG. 2D), proportional to the effects of eliminating 50% of the gene dosage. ALepflox-HZ mice display an increase in circulating adiponectin levels after 8-weeks of HFD (FIG. 2E). In line with our previous observations, following Dox-HFD feeding, ALepflox-HZ mice display a significant reduction in body weight gain, concomitant with a significant improvement in glucose tolerance (FIG. 2F-G). Of particular note, ALepflox-HZ mice do not display the conventional "whitening" of brown-fat (FIG. 2H), and display a reversal in HFD-induced hepatic steatosis (FIG. 2I). Our data thus fully support the observations made using Cas9-sgLeptin mice, confirming that a partial reduction of plasma leptin levels in the adult is beneficial in the context of obesity.

In the absence of leptin resistance, leptin effectively reduces food-intake and increases energy expenditure (Friedman, 2016). 8-week old, young and lean chow-fed mice maintain high levels of leptin sensitivity. As such, reducing leptin levels in lean chow-fed mice could serve as a valid model to verify our ALepKO mice. We therefore utilized chow diet containing the standard dose of DOX600 (600 mg/kg) to induce complete leptin gene deletion and observe that the circulating levels of leptin were greatly reduced by more than 90% (FIG. 6A). As expected, under these conditions of high leptin sensitivity at baseline with Dox-chow feeding, reducing leptin levels in ALepKO mice resulted in body weight gain, with associated worsened glucose tolerance and reduced insulin sensitivity (FIG. 6B-D). As such, this mouse model follows the "classical" model, whereby maximal leptin sensitivity is present and reducing leptin triggers a further lowering of leptin signaling centrally.

We then performed a more detailed set of experiments on HFD-fed animals. We used two different concentrations of DOX in HFD that we anticipated would allow us to go from near complete elimination of leptin, to a partial reduction in leptin. The high dose of DOX600-HFD feeding (600 mg/kg of Dox) triggers a rapid and significant increase in body weight gain over the 6-week period following initiation of leptin gene disruption (FIG. 3A). Conversely, at a much lower dose (DOX10), we observe a significant reduction in body weight gain over the course of a 6-week follow up period (FIG. 3B). Before DOX induction, ALepKO and Ctrl mice show similar leptin level (FIG. 3C). After DOX induction, the two different doses of Dox achieve a corresponding dose-dependent proportional reduction in plasma leptin levels in AlepKO mice (FIGS. 3C and 3D). It is interesting to notice that ALepKO mice on HFD-DOX600 rapidly increased body weight within first 3 weeks, followed by reduced body weight gain in the next 5 weeks, and this is different from classical ob/ob mice and could be partially explained by existing 10% leptin in circulation. Consistent with the body weight phenotype, ALepKO mice on DOX600 display no difference in glucose tolerance, slightly reduced insulin sensitivity and whitened brown fat (FIGS.

3E, 3G and 3I). In contrast, ALepKO mice on a DOX10 diet show beneficial effects on glucose metabolism and insulin sensitivity, with a reduction in the degree of "whitened" brown-fat (FIGS. 3F, 3H and 3J). The latter represents a phenotype similar to that what we observe for our ALepflox-HZ mice during high-dose Dox-HFD (600 mg/kg of Dox) feeding (FIGS. 2E and 2F). Collectively, this further demonstrates that a partial reduction, not a complete elimination of leptin, yields a completely unexpected, unique and, previously undescribed body weight phenotype.

In order to elucidate the mechanism of this unique body weight phenotype based on a partial reduction of leptin, ALepKO mice fed DOX10-HFD were placed into metabolic cages. Following partial leptin reduction, ALepKO mice increase their oxygen-consumption rates, both during the light and dark cycles over 5 days of recording (FIG. 3K and FIG. 6E). In addition, locomotor activity is significantly increased in ALepKO mice during both cycles (FIG. 3L and FIG. 6F). Finally, a moderate decrease in the respiratory exchange ratio (RER) is apparent during the dark cycle (FIG. 6G); reflecting a shift towards free fatty acid as a major energy source. However, the changes in the RER, in addition to other metabolic cage parameters, do not reach statistical significance (FIGS. 6G-6H). In addition, increased UCP-1 and PGC1-α were observed in sWAT and brown fat. Collectively, these results indicate that animal with a partial reduction in circulating levels of leptin display enhanced energy expenditure and locomotor activity, which is characteristic of a system with enhanced leptin sensitivity.

To further confirm our unique findings based on a partial leptin reduction, we first eliminated leptin gene expression in ALepKO mice by placing them on a chow-diet containing the standard dose of DOX600 for 1-week. ALepKO mice were then switched to a HFD lacking DOX. By utilizing this strategy, we achieved approximately half of the circulating levels of leptin evident in control mice, measured after 8 weeks' HFD (FIG. 6I). Although we appreciate that a portion of adipocytes will differentiate de novo under these conditions (and will carry WT copies of the leptin gene), these mice continue to display a partial leptin deficiency (Ctrl at 40 ng/ml, ALepKO at 19 ng/ml). Consistent with our previous findings, the mice here also display a significant reduction in body weight gain, concomitant with a marked improvement in glucose tolerance (FIG. 6J-6K).

As obesity triggers high circulating levels of leptin and is closely associated with leptin resistance, it is of great interest to examine whether a partial leptin deletion in obese mice can reverse the obesity-associated metabolic syndrome, post hoc HFD-induced metabolic dysfunction. To achieve this, ALepKO and control mice were placed on HFD (without Dox) for 6-weeks, and as expected, under baseline conditions, ALepKO mice and control littermates gain comparable body weight and display similar circulating levels of leptin (FIG. 6M). Following 6-weeks of HFD feeding, mice were then switched to the low-dose of Dox-HFD (10 mg/kg of Dox) to initiate a partial reduction of leptin in ALepKO mice. ALepKO mice display an approximate 50% reduction in plasma leptin levels (FIG. 6L). Furthermore, ALepKO mice fail to further gain more body weight and exhibited greatly improved glucose tolerance (FIGS. 6M and 6N). Combined, these results further confirm that hyperleptinemia per se is a major driving force for metabolic dysfunction, and a partial reduction of circulating leptin provides an effective strategy to overcome obesity and associated metabolic dysfunction.

Neutralizing Leptin Antibodies Confer Body Weight Gain Reduction

Given a partial reduction in the circulating levels of leptin in the context of obesity produces beneficial effects by improving glucose homeostasis, we began to generate neutralizing monoclonal antibodies against human leptin. We generated a large number of different monoclonal antibodies that exhibit leptin neutralizing activity, and describe below exemplary in vivo studies for three (hLep2, hLep3 and hLep5) (FIG. 7A).

We treated a cohort of obese mice either with vehicle or the three neutralizing antibodies. As shown in FIG. 7B, vehicle-treated mice exhibit a gradual increase in body weight, while mice treated with the three neutralizing antibodies display various levels of reduced body weight gain. hLep3 displays the most potent effects. In addition, none of the mice show differences in glucose tolerance prior to treatment (FIG. 7C). Following 2-weeks of antibody treatment, hLep3 and Lep5-treated mice show enhanced glucose tolerance, concomitant with a profound reduction in gonadal fat-pad weight, while hLep2-treated mice show no or little effect (FIGS. 7C and 7D). Based on this initial characterization, the hLep3 neutralizing antibody was selected for further experimental studies.

In order to rule out of possible endotoxin-induced weight loss, we performed similar study on obese mice with the isotype control antibody, a human IgG1 monoclonal antibody that we identified in house against human cytomegalovirus (hCMV virus). We generated and purified control antibody and hLep3 antibody with the same procedures. After two weeks' treatment, hLep3-treated significantly reduced body weight gain (FIG. 4A-B) and food intake (FIG. 4C). In addition, before antibody injection, there was no any difference in glucose tolerance and total fat mass (FIGS. 4D and 4F). hLep3 treatment greatly increased glucose tolerance (FIG. 4E) and significantly reduced fat mass (FIG. 4F). These results indicate that the beneficial effects is indeed originated from leptin neutralizing antibody.

To gain further insights into the possible causes that lead to the beneficial effects, vehicle or hLep3-treated mice were placed in metabolic cages. Following hLep3 treatment, we achieved a 50% reduction in circulating free leptin levels (FIG. 7F). As a consequence, hLep3-treated mice reduce food-intake (FIG. 4G) and show a significant reduction in the respiratory exchange ratio (RER) (FIG. 4H), without any significant differences apparent in locomotor activity (FIG. 7K-7L).

HFD feeding typically affects brown-fat in a negative manner, which results in a high degree of "whitened" BAT. This deterioration in BAT quality and function was prevented (in fact reversed) with leptin antibody treatment (FIG. 4I). Consistent with the histology, the gene expression levels of thermogenic genes, such as Ucp1 and Pgc1□, are significantly upregulated in sWAT and BAT of leptin antibody-treated mice (FIGS. 7G and 7H). With regards to the liver, we observe a marked reduction in diet-induced hepatic steatosis following antibody treatment (FIG. 4J). In adipose tissue itself, hLep3-treatment reduces the degree of adipose tissue inflammation and reduces the average adipocyte size (FIGS. 7I-7J). Taken together, these results confirm that a partial reduction in the circulating levels of leptin, through the use of neutralizing antibodies, leads to a reduction in food-intake and a re-activation of the thermogenic program in brown-fat, collectively revealing a model of restored leptin sensitivity.

In order to deconvolute the relative contribution of food-intake and non-shivering thermogenesis in the context of body weight reduction, we treated obese WT mice with vehicle or hLep3 antibody under thermoneutral conditions (to minimize the effects of non-shivering thermogenesis). Upon thermoneutral housing, hLep3-treated obese mice effectively reduce their body weight gain and preserve their glucose tolerance (FIG. 4K), even in the absence of any notable brown fat activity (FIG. 7M-7N). Thermoneutral housing is a strong additive factor to further promote liver steatosis and fibrosis during HFD feeding. Surprisingly, hLep3 treatment of mice effectively reverse diet-induced hepatic steatosis, as evident by less hepatic lipid droplet accumulation, even under these thermoneutral conditions (FIG. 7O). Taken together, our results indicate that the neutralizing leptin antibodies retain their full beneficial effects even under thermoneutral conditions. Moreover, it is predominantly the reduction in food-intake that contributes towards the observed unique body weight phenotype. As an additional control, we administered Lep3 mAb and vehicle in ob/ob mice that do not have functional leptin, the Lep3 mAb shows no effect on weight gain and lacks any efficacy compared to a WT control (FIG. 4L). These results further demonstrate that Lep3 mAb functions exclusively on the basis of a reduction in systemic leptin levels.

Partial Leptin Deficiency in Obese Mice Reverses Leptin Resistance

The data so far indicates that a partial deletion in leptin leads to reduced food-intake and enhanced adaptive thermogenesis, which is consistent with an enhanced degree of leptin sensitivity. As such, this prompted us to search for further evidence demonstrating "restored" leptin sensitivity in obese mice. To this end, we first examined leptin sensitivity in leptin transgenic mice. As observed in FIGS. 8A and 8B, the expression of Pomc and Agrp in the mediobasal hypothalamus (MBH) region of the brain is significantly reduced in Alep-TG mice, compared with control mice. In contrast, the gene expression levels of Socs3, Tnfα and interleukin-1β are significantly increased; indicative of a higher degree of leptin resistance associated with hypothalamic inflammation (FIG. 8C-8F).

In contrast to Alep-TG mice, a partial reduction in leptin, as achieved through genetic deletion or by utilizing neutralizing antibodies, leads to improvements in the MBH region of the brain; as reflected by increased Pomc expression and decreased Socs3 expression (FIGS. 5A, 5B, 5F and 5G). Inflammation in the MBH region is ameliorated in ALepKO mice, as reflected by a reduction in Tnfα and interleukin-1β expression (FIGS. 8G and 8H). In line with these observations, following oral gavage of Dox at a dose of 5 mg/kg body weight to induce partial ob gene deletion, ALepKO mice exhibit a reduction in food-intake, with higher basal food-intake evident compared to vehicle treatment (FIG. 5C); consistent with enhanced leptin sensitivity. Moreover, following acute injection of leptin, ALepKO mice exhibit a greater reduction in food-intake at multiple different time-points (2 hr, 4 hr, 8 hr and 24 hr) (FIG. 5D). Interestingly, immunohistochemical staining reveals a marked increase in p-STAT3 in ALepKO mice, or upon treatment of obese mice with neutralizing antibodies (FIGS. 5E and 5H). In addition, long-term treatment with neutralizing anti-mouse leptin antibodies (6 weeks) triggers a 10% reduction in food-intake. Importantly, this reduction could be maintained for several weeks, without any loss of effectiveness of the treatment due to "de-sensitization" to the antibody (FIG. 5I). This indicates that this approach provides an effective long-term weight loss strategy. In fact, genetic reduction of leptin levels in the adult mouse results in the maintenance of the effects reported for more than 10 months (FIG. 8L), emphasizing that there is no "re-calibration" of homeostatic control of fat-mass upon leptin reduction if the leptin reduction is performed in the adult animal.

In order to further confirm enhanced leptin sensitivity induced through reduction of leptin levels, we treated HFD-fed POMC-hrGFP::LepR-cre::tdtomato mice (Sun et al., 2016) with neutralizing leptin antibodies. POMC neurons were then targeted for whole-cell patch-clamp recordings, for which arcuate POMC neurons with or without the expression of leptin receptors could be identified (FIG. 5J-5N). HFD feeding blunts the acute leptin-induced depolarization of leptin receptor-expressing POMC neurons, when compared with chow-diet fed mice (100 nM, chow-diet fed: 7/10, change of resting membrane potential: 6.9±0.6 mV; HFD fed: 7/12, change of resting membrane potential: 3.7±0.4 mV, p<0.001, FIGS. 5O and 5P). Importantly, leptin antibody treatment of HFD-fed mice restores the acute effects of leptin to depolarize leptin receptor-expressing POMC neurons (100 nM, 9/12, change of resting membrane potential: 7.2±0.8 mV, p<0.01, FIG. 5Q). These data illustrate that HFD leads to a blunting of the acute leptin effects in leptin receptor-expressing POMC neurons, while the neutralizing antibody can restore acute leptin action in leptin receptor-expressing POMC neurons (FIG. 5R). In addition to the enhanced leptin sensitivity evident in the central nervous system (CNS), peripheral tissues also exhibit a higher degree of leptin sensitivity. The mRNA levels of hormone-sensitive lipase (HSL) and the protein levels of p-HSL (but not ATGL) in visceral fat is greatly increased in ALepKO mice (FIGS. 8I-8K). Taken together, these results further demonstrate that partial leptin reduction enhances leptin sensitivity during obesity.

Discussion

We take advantage of our recently developed genetic models of inducible gene elimination in the adult setting to examine leptin action in the context of an otherwise unchanged adipocyte; The initial manipulation of leptin leaves all other adipocyte-derived factors unaltered, at least at the early stages of the process. In other words, in contrast to conventional methods that involve severe weight loss or massive weight gain to alter leptin levels, we describe here a downwards titration of leptin levels at the level of the adult, effectively reducing bioavailable leptin concentrations that reach the hypothalamus. We are doing this without initially affecting the adipocyte in any other way. This novel experimental paradigm has in fact not been pursued previously, and as such, has allowed us to observe unexpected effects that are consistent with an abrupt sensitization to the actions of leptin: low leptin to high leptin→leptin resistance; high leptin to low leptin→leptin sensitivity, i.e. With adipose tissue expansion, high leptin levels are achieved in circulation, leading to high degree of leptin resistance; and reducing leptin levels in a setting of high circulating leptin restores leptin sensitivity.

Up to date, two prevailing models are proposed to explain leptin action in the brain, summarized in a recent review (Flier, 2018). In the first model, adipocytes-produced leptin in circulation is proportionally elevated with increased fat mass and triggers a response in critical hypothalamic neuronal populations, which ultimately prompts a corresponding increase in energy expenditure with a reduction in food-intake (Flier, 2018). Overall, this establishes a model of homeostatic control over specific energy reserves and fat mass. An alternative model argues that the primary signal sensed centrally is not an increase in circulating leptin levels. Rather, the relevant signal is a decrease in circulating leptin levels that signals an energy deficit. This drop in leptin levels leads to a decrease in food-intake and a reduction in energy expenditure. In both models, the central sensing mechanism critically relies on changes in circulating leptin concentrations. All the leptin action relies on the presence of functional leptin receptors in the brain and peripheral tissues (Clement et al., 1998). Reducing or eliminating leptin receptor activity by genetic mutation or with a pharmacological receptor antagonist leads to severe obesity in mice. In the obese setting, a leptin receptor antagonist can still produce an increased body weight gain and food intake. This leads to the conclusion that diet-induced obese mice retain near maximum endogenous leptin action (Ottaway et al., 2015). However, a recent report indicates that central inhibition of leptin receptor in diet-induced obese mice improves glucose tolerance and hepatic insulin sensitivity (Balland et al, Cell Rep. 2019 Jan. 8; 26(2):346-355.e3), which favors our current partial leptin reduction strategy. Further study indicates that leptin signaling in the arcuate nucleus of the hypothalamus of obese mice not only remains functional, but is constantly activated. As a result of this persistent activation to endogenous high circulating leptin, it leads to saturation of leptin signaling and lacks further reaction to exogenous leptin. The lack of anorexic effects in the presence of persistent leptin signaling in the ARH lies in the existence of the potent feedback mechanisms by inducing suppressor of cytokine signaling 3 (SOCS3) and protein tyrosine phosphatases (PTP1B) expression to block leptin signaling cascade. Of special interest, SOCS3 expression in the ARH area is leptin-dependent: higher leptin induces higher SOCS3 expression. Our results indicate that partial leptin reduction via genetic manipulation and leptin neutralizing antibody reduce SOCS3 expression. Furthermore, PTP1B exerts its inhibitory effect on both leptin and insulin signaling pathway to promote obesity and type 2 diabetes. Thus, in the context of obesity, the major cause of the lack of leptin action is not the defect in leptin signaling, but indeed the potent feedback mechanisms induced by constitutive activation of leptin signaling. Partial leptin reduction in the ARH ameliorates feedback mechanism of leptin signaling and restores leptin sensitivity.

In the context of obesity, hyperleptinemia (Knight et al., 2010), excess circulating lipids (Banks et al., 2004), and inflammation (Myers et al., 2010) are all proposed to be driving forces to induce leptin resistance. However, our data indicate that leptin resistance primarily stems from high circulating leptin levels, as circulating lipids and inflammation are both shown to stimulate leptin secretion. In clinical studies, a subset of obese individuals is shown to possess very low levels of circulating leptin. Accordingly, these obese subjects should retain higher level of leptin sensitivity and respond especially well to exogenous leptin treatment. Similarly, partial leptin reduction by weight-loss in humans expectedly leads to higher leptin sensitivity. In that case, low-dose leptin treatment should potentiate the physiological action of leptin, resulting in reversing skeletal muscle, autonomic and neuroendocrine adaptations. One recent study directly examined whether negative energy balance signals could counteract participants' efforts to continue losing weight by increasing food cue reactivity and food intake. They concluded that reduction in leptin does not counteract weight loss, and it is indeed correlated with further weight loss in a long term (Neseliler et al. Cell Metab. 2019 Jan. 8; 29(1):39-49.e4). These observations show that the beneficial effects of partial leptin deletion not only occur in rodents, but also in humans.

In previous studies, partial leptin deficiency, achieved by the congenital deletion of one copy of ob (gene $ob^{-/+}$ mice) or by dysregulation of a long noncoding RNA (lncOb) is associated with accelerated weight gain and impaired glucose tolerance (Begriche et al., 2008; Farooqi et al., 2001); which is in contrast to our current findings. However, the strategy applied in these studies relies on a congenital elimination of ob or lncOb gene during development, rather than the inducible gene deletion at the adult age that we utilize here. The leptin surge during development is crucial for the maturation and function of the neuroendocrine axis (Delahaye et al., 2008). In addition, the actual circulating levels of leptin detected in the adult $ob^{-/+}$ mouse are not decreased, rather increased. Thus, this model cannot be considered to be an effective "partial leptin deficiency model", but rather resembles a model of physiologically increased leptin levels; comparable to what we show in our leptin transgenic mice. In addition, for mice deficient in lncOb, it is still unclear whether dysregulation of lncOb in mice will affect other gene expressions, as deletion of lncOb in female mice produces more profound effects in body weight.

Another important concern relates to the effects of leptin on fertility (Barash et al., 1996; Chehab et al., 1996). Complete lack of leptin action triggers infertility, since it reflects insufficient fat mass to undergo successful reproduction. There is a legitimate concern that our approach reducing leptin levels may reduce or completely abolish fertility. We tested this in the context of our inducible genetic loss of function model in which we reduced leptin levels by 90% on a high fat diet, and we saw no impact on fertility at all, with an equal number of pregnancies initiated, and a comparable number of pups and viability.

The pharmacological reduction of leptin under obese conditions, through the use of neutralizing antibodies, provides not only a weight loss strategy, but also useful antidiabetic properties associated with the ability to titrate down effective leptin concentrations in plasma.

REFERENCES AND NOTES

Ahima, R. S., and Flier, J. S. (2000). Leptin. Annu Rev Physiol 62, 413-437.
Banks, W. A., et al (2004). Triglycerides induce leptin resistance at the blood-brain barrier. Diabetes 53, 1253-1260.
Barash, I. A., et al. (1996). Leptin is a metabolic signal to the reproductive system. Endocrinology 137, 3144-3147.
Begriche, K., et al. (2008). Partial leptin deficiency favors diet-induced obesity and related metabolic disorders in mice. Am J Physiol Endocrinol Metab 294, E939-951.
Caro, J. F., et al. (1996). Decreased cerebrospinal-fluid/serum leptin ratio in obesity: a possible mechanism for leptin resistance. Lancet 348, 159-161.
Chehab, F. F., Lim, M. E., and Lu, R. (1996). Correction of the sterility defect in homozygous obese female mice by treatment with the human recombinant leptin. Nat Genet 12, 318-320.
Clement, K., et al. (1998). A mutation in the human leptin receptor gene causes obesity and pituitary dysfunction. Nature 392, 398-401.
Delahaye, F., et al (2008). Maternal perinatal undernutrition drastically reduces postnatal leptin surge and affects the development of arcuate nucleus proopiomelanocortin neurons in neonatal male rat pups. Endocrinology 149, 470-475.

Farooqi, I. S., et al. (1999). Effects of recombinant leptin therapy in a child with congenital leptin deficiency. N Engl J Med 341, 879-884.

Farooqi, I. S., et al. (2001). Partial leptin deficiency and human adiposity. Nature 414, 34-35.

Flier, J. S. (2018). Starvation in the Midst of Plenty: Reflections on the History and Biology of Insulin and Leptin. Endocr Rev.

Flier, J. S., and Maratos-Flier, E. (2017). Leptin's Physiologic Role: Does the Emperor of Energy Balance Have No Clothes? Cell Metab 26, 24-26.

Friedman, J. (2016). The long road to leptin. J Clin Invest 126, 4727-4734.

Friedman, J. M., and Halaas, J. L. (1998). Leptin and the regulation of body weight in mammals. Nature 395, 763-770.

Halaas, J. L., Boozer, C., Blair-West, J., Fidahusein, N., Denton, D. A., and Friedman, J. M. (1997). Physiological response to long-term peripheral and central leptin infusion in lean and obese mice. Proc Natl Acad Sci USA 94, 8878-8883.

Hausman, G. J., Barb, C. R., and Lents, C. A. (2012). Leptin and reproductive function. Biochimie 94, 2075-2081.

Knight, Z. A., Hannan, K. S., Greenberg, M. L., and Friedman, J. M. (2010). Hyperleptinemia is required for the development of leptin resistance. PLoS One 5, e11376.

Koch, C. E., Lowe, C., Pretz, D., Steger, J., Williams, L. M., and Tups, A. (2014). High-fat diet induces leptin resistance in leptin-deficient mice. J Neuroendocrinol 26, 58-67.

Kusminski, C. M., Bickel, P. E., and Scherer, P. E. (2016). Targeting adipose tissue in the treatment of obesity-associated diabetes. Nat Rev Drug Discov 15, 639-660.

Kusminski, C. M., Park, J., and Scherer, P. E. (2014). MitoNEET-mediated effects on browning of white adipose tissue. Nat Commun 5, 3962.

Mark, A. L. (2013). Selective leptin resistance revisited. Am J Physiol Regul Integr Comp Physiol 305, R566-581.

Mittendorfer, B., et al. (2011). Recombinant human leptin treatment does not improve insulin action in obese subjects with type 2 diabetes. Diabetes 60, 1474-1477.

Montague, C. T., et al. (1997). Congenital leptin deficiency is associated with severe early-onset obesity in humans Nature 387, 903-908.

Moon, H. S., et al. (2011). Efficacy of metreleptin in obese patients with type 2 diabetes: cellular and molecular pathways underlying leptin tolerance. Diabetes 60, 1647-1656.

Myers, M. G., Jr., Leibel, R. L., Seeley, R. J., and Schwartz, M. W. (2010). Obesity and leptin resistance: distinguishing cause from effect. Trends Endocrinol Metab 21, 643-651.

Nunziata, A., et al. (2019). Functional and Phenotypic Characteristics of Human Leptin Receptor Mutations. J Endocr Soc 3, 27-41.

Ogawa, Y., Masuzaki, H., Ebihara, K., Shintani, M., Aizawa-Abe, M., Miyanaga, F., and Nakao, K. (2002). Pathophysiogical role of leptin in lifestyle-related diseases. Studies with transgenic skinny mice overexpressing leptin. J Diabetes Complications 16, 119-122.

Ottaway, N., et al. (2015). Diet-induced obese mice retain endogenous leptin action. Cell Metab 21, 877-882.

Savoye, M., Dziura, J., Castle, J., DiPietro, L., Tamborlane, W. V., and Caprio, S. (2002). Importance of plasma leptin in predicting future weight gain in obese children: a two-and-a-half-year longitudinal study. Int J Obes Relat Metab Disord 26, 942-946.

Scherer, P. E. (2016). The Multifaceted Roles of Adipose Tissue-Therapeutic Targets for Diabetes and Beyond: The 2015 Banting Lecture. Diabetes 65, 1452-1461.

Shimomura, I., Hammer, R. E., Ikemoto, S., Brown, M. S., and Goldstein, J. L. (1999). Leptin reverses insulin resistance and diabetes mellitus in mice with congenital lipodystrophy. Nature 401, 73-76.

Sun, J., et al. (2016). Adiponectin potentiates the acute effects of leptin in arcuate Pomc neurons. Mol Metab 5, 882-891.

Van Heek, M., et al (1997). Diet-induced obese mice develop peripheral, but not central, resistance to leptin. J Clin Invest 99, 385-390.

Zelissen, P. M., et al. (2005). Effect of three treatment schedules of recombinant methionyl human leptin on body weight in obese adults: a randomized, placebo-controlled trial. Diabetes Obes Metab 7, 755-761.

Zeltser, L. M. (2015). Developmental influences on circuits programming susceptibility to obesity. Front Neuroendocrinol 39, 17-27.

Zhu, Y., et al. (2016). Connexin 43 Mediates White Adipose Tissue Beiging by Facilitating the Propagation of Sympathetic Neuronal Signals. Cell Metab 24, 420-433.

What is claimed is:

1. A method of treating obesity, the method comprising administering to an obese person a therapeutic leptin neutralizing monoclonal antibody, wherein the antibody effects a partial inhibition of circulating leptin in the person.

2. The method of claim 1, further comprising detecting a resultant improvement of the obesity in the person.

3. The method of claim 1, further comprising detecting a resultant improvement of the obesity in the person, that is a decrease in body weight of the person.

4. The method of claim 1, further comprising detecting the resultant partial inhibition of circulating leptin in the person.

* * * * *